US 6,664,066 B2

(12) United States Patent
Parks

(10) Patent No.: US 6,664,066 B2
(45) Date of Patent: Dec. 16, 2003

(54) MODIFIED MORBILLIVIRUS V PROTEINS

(75) Inventor: Christopher L. Parks, Boonton, NJ (US)

(73) Assignee: Wyeth Holdings Corporation, Madison, NJ (US)

( * ) Notice: Subject to any disclaimer, the term of this patent is extended or adjusted under 35 U.S.C. 154(b) by 0 days.

(21) Appl. No.: 10/311,582

(22) PCT Filed: Jun. 21, 2001

(86) PCT No.: PCT/US01/19806

§ 371 (c)(1),
(2), (4) Date: Dec. 16, 2002

(87) PCT Pub. No.: WO02/00694

PCT Pub. Date: Jan. 3, 2002

(65) Prior Publication Data

US 2003/0206925 A1 Nov. 6, 2003

Related U.S. Application Data

(60) Provisional application No. 60/213,655, filed on Jun. 23, 2000.

(51) Int. Cl.[7] .............................. C12Q 1/68; C12Q 1/70;
A61K 39/38; A61K 39/12; C07H 21/04
(52) U.S. Cl. ............................ 435/6; 435/5; 424/184.1;
424/199.1; 536/23.72
(58) Field of Search ....................... 435/5, 6; 424/184.1,
424/199.1; 536/23.72

(56) References Cited

FOREIGN PATENT DOCUMENTS

| EP | 0702085 A1 | 3/1996 |
|----|------------|--------|
| WO | WO 97/06270 A1 | 2/1997 |
| WO | WO 98/13501 A2 | 4/1998 |
| WO | WO 98/53078 A1 | 11/1998 |
| WO | WO 99/49017 A2 | 9/1999 |

OTHER PUBLICATIONS

Nagai, Y., *Rev. Med. Virol. 9*, 83–99, (1999).
Baron, M.D., and Barrett, T., *J. Virol.*, 74, 2603–2611, (2000).
Delenda, C., et al., *Virology*, 242, 327–337, (1998).
Durbin, A.P., et al., *Virology*, 261, 319–330, (1999).
Kato, A., et al., *J. Virology*, 71, 7266–7272, (1997).
Schneider, H., et al., *Virology*, 227, 314–322, (1997).
Kato, A., et al., *EMBO J.*, 16, 578–587, (1997).
Tober, C., et al., *J. Virol.*, 72, 8124–8132, (1998).
Valsamakis, A., et al., *J. Virology.*, 72, 7754–7761, (1998).
Patterson, J.B., et al., *Virology.*, 267, 80–89, (2000).
Parks, C.L., et al., *J. Virol.*, 75, 910–920, (2001).
Harty, R.N., and Palese, P., *J. Gen Virol.*, 76, 2863–2867, (1995).
Horikami, S.M., et al., *Virology*, 222, 383–390, (1996).
Curran, J., et al., *EMBO J.*, 10, 3079–3085, (1991).
Baron, M.D., et al., *J. Gen. Virol.*, 74, 299–304, (1993).
Liston, P., and Briedis, D. J., *Virology*, 198, 399–404 (1994).
Parks, C.L., et al., *J. Virol.*, 75, 921–933, (2001).
Moss, B., et al., *Nature*, 348, 91–92, (1990).
Wyatt, L.S., et al., *Virology*, 210, 202–205, (1995).
Sidhu, M.S., et al., *Virology*, 208, 800–807, (1995).
Huber, M. et al., *Virology*, 185, 299–308, (1991).
Alber, T., *Curr. Opin. Genetics Dev.*, 2, 205–210, (1992).

(List continued on next page.)

*Primary Examiner*—Hankyel T. Park
(74) *Attorney, Agent, or Firm*—Alan M. Gordon; Carol E. Rozek

(57) ABSTRACT

Modified Morbilliviruses having at least one mutation in the region corresponding to amino acids 112–134 of the measles virus V protein are described, wherein one or both of amino acids 113 or 114 is mutated. Such modified Morbilliviruses exhibit reduced repression of gene expression. Additional mutations or deletions in other regions of the genome may be included, including in the carboxy-terminal region.

34 Claims, 15 Drawing Sheets

OTHER PUBLICATIONS

Baxevanis, A.D., and Vinson, C. R., *Curr. Opion. Genetics Dev., 3*, 278–285, (1993).

Kolodziej, P.A., and Young, R.A., *Methods Enzymology, 194*, 508–519 (1991).

Bass, S.H., et al., *Proc. Natl. Acad. Sci., USA, 88*, 4498–4502, (1991).

Diamond, S.E., and Kirkegaard, K., *J. Virol., 68*, 863–876, (1994).

Gibbs, C.S., and Zoller, M.J., *J. Biol. Chem., 266*, 8923–8931, (1991).

Giniger, E., and Ptashne, M., *Nature, 330*, 670–672, (1987).

Sedlmeirer, R., and Neubert, W. J., *Adv. Virus Res., 50*, 101–139, (1998).

Lin, G.Y., et al., *Virology, 238*, 460–469, (1997).

Elenbaas, B., et al., *Molecular Medicine, 2*, 439–451, (1996).

Kiledjian, M., and Dreyfuss, G., *EMBO J., 11*, 2655–2664, (1992).

Siomi, H., et al., *Cell, 74*, 291–298, (1993).

Swanson, M., and Dreyfuss, G., *Mol. Cell Biol., 8*, 2237–2241, (1988).

Mitchell, P., and Tjian, R., *Science, 245*, 371–378 (1989).

Conzelmann, DK. K., *Annual Review of Genetics, 32*, 123–162 (1998).

Radecke, F., and Billeter, M.A., *Rev. Med. Virology, 7*, 49–63, (1997).

Roberts, A., and Rose, J.K., *Virology, 247*, 1–6, (1998).

Garcin, D., et al., *EMBO J., 14*, 6087–6094 (1995).

Radecke, F., et al., *EMBO J., 14*, 5773–5784 (1995).

Collins, P. L., et al., *Proc. Natl. Acad. Sci., USA, 92*, 11563–11567, (1995).

Rota, J.S., et al., *Virus Res., 31*, 317–330, (1994).

Baron, M.D., and Barrett, T., *J. Virology, 71*, 1265–1271 (1997).

Kato, A., et al., *Genes to Cells, 1*, 569–579, (1996).

Shaffer, M.F., et al., *J. Immunol., 41*, 241–256, (1941).

Enders, J. F., et al., *N. Engl. J. Med., 263*, 153–159 (1960).

Chomczynski, P., and Sacchi, N., *Analytical Biochem., 162*, 156–159 (1987).

Parks, C.L., et al., *J. Virol., 73*, 3560–3566 (1999).

```
              CR1        10                      20
          ┌─────────────────────────────────────────┐
     1    │ M A E E Q A R H V K N G L E C I R A L K │ MV
     1    │ M A E E Q A Y H V N K G L E C I K A L R │ RPV
     1    │ M A E E Q A Y H I N K G L E C L K S L R │ DMV
     1    │ M A E E Q A Y H V S K G L E C L K A L R │ CDV
          └─────────────────────────────────────────┘
           (P/V)-N interaction 30                      40
     21    A E P I G S L A I E E A M A A W S E I S   MV
     21    A R P L D P L V V E E A L A A W V E T S   RPV
     21    E N P P D A V E I K E A Q I I R S K A A   DMV
     21    E N P P D I E E I Q E V S S L R D Q T C   CDV 50                      60
     41    D N P G Q E R A T C R E E K A G S S G L   MV
     41    E G Q T L D R M S S D E A E A D H Q D I   RPV
     41    C E E S S E H H Q D N S E K D T L D F     DMV
     41    N P G Q E N G T G M Q E E E D S Q N L     CDV 70                      80
     61    S K P C L S A I G S T E G G A P R I R G   MV
     61    S K P C F P A A G P G K S S M S R C H D   RPV
     61    D E S C S S A I R P E T Y R M L L G D D   DMV
     61    D E S H E P T K G S N Y V G H V P Q N N   CDV 90           MV Leu repeat
     81    Q G P G E S D D D A E T L G - - I P P R   MV
     81    Q G L R G S N S C D E E L G A F I G D S   RPV
     81    T G F R A P G Y I P N E G E P - - E P G   DMV
     81    P G C G E R N T A L V E A E R - - P P R   CDV 100              110        CR2>
     99    N L Q A S S T G L Q C Y Y V Y D H S G E   MV
     101   S M H - - S T E V Q H Y H V Y D H S G E   RPV
     99    D I G K E E P A V R C Y H V Y D H G G Q   DMV
     99    E D I Q P G P G I R C D H V Y D H S G E   CDV
```

FIG.2A

```
          120       <CR2    130
      119 A V K G I Q D A D S I M V Q S G L D G D  MV
      119 K V E G V E D A D S I L V Q S G A D D G  RPV
      119 A V E G V K D A D L L V V P T G S D D D  DMV
      119 E V K G I E D A D S L V V P A G T V G N  CDV 140              150
      139 S T L S G G D N E S E N S D V D I G E P  MV
      139 V E V W G G D E E S E N S D V D S G E P  RPV
      139 A E F R D G D E S S L E S D G E S G T V  DMV
      139 R G F E R G E G S L D D S T E D S G E D  CDV 160              170           CR3>
      159 D T E G Y A I T D R G S A P I S M G F R  MV
      159 D P E G S A P A D W G S S P I S P A T R  RPV
      159 D T R G N S S S N R G S A P R I K V E R  DMV
      159 Y S E G N A S S N W G Y S F G L K P D R  CDV

180 CR3          190
      179 A S D V E T A E G G E I H E L L R L Q S  MV
      179 A S D V E T V E G D E I Q K L L E D Q S  RPV
      179 S S D V E T I S S E E L Q G L I R S Q S  DMV
      179 A A D V S M L M E E E L S A L L R T S R  CDV 200              210 CR4
      199 R G N N F P K L G K T L N V P P P P D P  MV
      199 R I R K M T K A G K T L V V P P I P S Q  RPV
      199 Q K H N G F G V D R F L K V P P I P T S  DMV
      199 N V G I Q K R D G K T L Q F P H N P E G  CDV
                               V-N complex localization >

220 mv vacs G     230           CR5>
      219 G R A S T S E T P I K K G H R R E I S L  MV
      219 E R P T A S E K P I K K G H R R E I D L  RPV
      219 V P L D P A P K S I K K G H R R E I S L  DMV
      219 K T R D P E C G S I K K G H R R E V S L  CDV
          < V-N complex localization
                             Basic
```

FIG.2B

```
         240 <CR5                250
          |                       |
239  I W N G D R V F I D R W C N P M C S K V   MV
239  I W N D G R V F I D R W C N P T C S K V   RPV
239  I W D G D R V F I D R W C N P T C S R I   DMV
239  T W N G D S C W I D K W C N P I C T Q V   CDV
                                  C   C

260             CR6    270
          |                       |
259  T L G T I R A R C T C G E C P R V C E Q   MV
259  T V G T V R A K C I C G E C P R V C E Q   RPV
259  K M G I V R V K C T C G E C P P V C D E   DMV
259  N W G I I R A K C F C G E C P P T C N E   CDV
     < Zn binding    C   C   C       C 280             290
               |               |
279  C R T D T G V D T R I W Y H N L P E I P   MV
279  C I T D S G I E N R I W Y H N L A D I P   RPV
279  C R E D P E T P T R I W Y H S L P E I P   DMV
279  C K D D P E M Q T R V W - - - - H A T P   CDV
     C 299  - - - - - E          MV
299  - - - - - E          RPV
299  E Q W P F -          DMV
295  S Q - D L K          CDV
```

FIG.2C

SEQUENCE LISTING

<160> NUMBER OF SEQ ID NOS: 24

<210> SEQ ID NO 1
<211> LENGTH: 299
<212> TYPE: PRT
<213> ORGANISM: Measles virus

<400> SEQUENCE: 1

| Met | Ala | Glu | Glu | Gln | Ala | Arg | His | Val | Lys | Asn | Gly | Leu | Glu | Cys | Ile |
|---|---|---|---|---|---|---|---|---|---|---|---|---|---|---|---|
| 1 | | | | 5 | | | | | 10 | | | | | 15 | |

| Arg | Ala | Leu | Lys | Ala | Glu | Pro | Ile | Gly | Ser | Leu | Ala | Ile | Glu | Glu | Ala |
|---|---|---|---|---|---|---|---|---|---|---|---|---|---|---|---|
| | | | 20 | | | | | 25 | | | | | 30 | | |

| Met | Ala | Ala | Trp | Ser | Glu | Ile | Ser | Asp | Asn | Pro | Gly | Gln | Glu | Arg | Ala |
|---|---|---|---|---|---|---|---|---|---|---|---|---|---|---|---|
| | | | 35 | | | | | 40 | | | | | 45 | | |

| Thr | Cys | Arg | Glu | Glu | Lys | Ala | Gly | Ser | Ser | Gly | Leu | Ser | Lys | Pro | Cys |
|---|---|---|---|---|---|---|---|---|---|---|---|---|---|---|---|
| | | 50 | | | | | 55 | | | | | 60 | | | |

| Leu | Ser | Ala | Ile | Gly | Ser | Thr | Glu | Gly | Gly | Ala | Pro | Arg | Ile | Arg | Gly |
|---|---|---|---|---|---|---|---|---|---|---|---|---|---|---|---|
| 65 | | | | | 70 | | | | | 75 | | | | | 80 |

| Gln | Gly | Pro | Gly | Glu | Ser | Asp | Asp | Ala | Glu | Thr | Leu | Gly | Ile | Pro |
|---|---|---|---|---|---|---|---|---|---|---|---|---|---|---|
| | | | | 85 | | | | | 90 | | | | | 95 |

| Pro | Arg | Asn | Leu | Gln | Ala | Ser | Ser | Thr | Gly | Leu | Gln | Cys | Tyr | Tyr | Val |
|---|---|---|---|---|---|---|---|---|---|---|---|---|---|---|---|
| | | | 100 | | | | | 105 | | | | | 110 | | |

| Tyr | Asp | His | Ser | Gly | Glu | Ala | Val | Lys | Gly | Ile | Gln | Asp | Ala | Asp | Ser |
|---|---|---|---|---|---|---|---|---|---|---|---|---|---|---|---|
| | | 115 | | | | | 120 | | | | | 125 | | | |

| Ile | Met | Val | Gln | Ser | Gly | Leu | Asp | Gly | Asp | Ser | Thr | Leu | Ser | Gly | Gly |
|---|---|---|---|---|---|---|---|---|---|---|---|---|---|---|---|
| 130 | | | | | 135 | | | | | 140 | | | | | |

| Asp | Asn | Glu | Ser | Glu | Asn | Ser | Asp | Val | Asp | Ile | Gly | Glu | Pro | Asp | Thr |
|---|---|---|---|---|---|---|---|---|---|---|---|---|---|---|---|
| 145 | | | | | 150 | | | | | 155 | | | | | 160 |

| Glu | Gly | Tyr | Ala | Ile | Thr | Asp | Arg | Gly | Ser | Ala | Pro | Ile | Ser | Met | Gly |
|---|---|---|---|---|---|---|---|---|---|---|---|---|---|---|---|
| | | | | 165 | | | | | 170 | | | | | 175 | |

| Phe | Arg | Ala | Ser | Asp | Val | Glu | Thr | Ala | Glu | Gly | Gly | Glu | Ile | His | Glu |
|---|---|---|---|---|---|---|---|---|---|---|---|---|---|---|---|
| | | | 180 | | | | | 185 | | | | | 190 | | |

| Leu | Leu | Arg | Leu | Gln | Ser | Arg | Gly | Asn | Asn | Phe | Pro | Lys | Leu | Glu | Lys |
|---|---|---|---|---|---|---|---|---|---|---|---|---|---|---|---|
| | | 195 | | | | | 200 | | | | | 205 | | | |

| Thr | Leu | Asn | Val | Pro | Pro | Pro | Pro | Asp | Pro | Gly | Arg | Ala | Ser | Thr | Ser |
|---|---|---|---|---|---|---|---|---|---|---|---|---|---|---|---|
| 210 | | | | | 215 | | | | | 220 | | | | | |

| Glu | Thr | Pro | Ile | Lys | Lys | Gly | His | Arg | Arg | Glu | Ile | Ser | Leu | Ile | Trp |
|---|---|---|---|---|---|---|---|---|---|---|---|---|---|---|---|
| 225 | | | | | 230 | | | | | 235 | | | | | 240 |

| Asn | Gly | Asp | Arg | Val | Phe | Ile | Asp | Arg | Trp | Cys | Asn | Pro | Met | Cys | Ser |
|---|---|---|---|---|---|---|---|---|---|---|---|---|---|---|---|
| | | | | 245 | | | | | 250 | | | | | 255 | |

| Lys | Val | Thr | Leu | Gly | Thr | Ile | Arg | Ala | Arg | Cys | Thr | Cys | Gly | Glu | Cys |
|---|---|---|---|---|---|---|---|---|---|---|---|---|---|---|---|
| | | | 260 | | | | | 265 | | | | | 270 | | |

| Pro | Arg | Val | Cys | Glu | Gln | Cys | Arg | Thr | Asp | Thr | Gly | Val | Asp | Thr | Arg |
|---|---|---|---|---|---|---|---|---|---|---|---|---|---|---|---|
| | | 275 | | | | | 280 | | | | | 285 | | | |

| Ile | Trp | Tyr | His | Asn | Leu | Pro | Glu | Ile | Pro | Glu |
|---|---|---|---|---|---|---|---|---|---|---|
| | 290 | | | | | 295 | | | | |

<210> SEQ ID NO 2
<211> LENGTH: 299
<212> TYPE: PRT
<213> ORGANISM: Rinderpest virus

<400> SEQUENCE: 2

| Met | Ala | Glu | Glu | Gln | Ala | Tyr | His | Val | Asn | Lys | Gly | Leu | Glu | Cys | Ile |
|---|---|---|---|---|---|---|---|---|---|---|---|---|---|---|---|
| 1 | | | | 5 | | | | | 10 | | | | | 15 | |

-continued

```
Lys Ala Leu Arg Ala Arg Pro Leu Asp Pro Leu Val Glu Glu Ala
             20                  25                  30

Leu Ala Ala Trp Val Glu Thr Ser Glu Gly Gln Thr Leu Asp Arg Met
         35                  40                  45

Ser Ser Asp Glu Ala Glu Ala Asp His Gln Asp Ile Ser Lys Pro Cys
     50                  55                  60

Phe Pro Ala Ala Gly Pro Gly Lys Ser Ser Met Ser Arg Cys His Asp
 65                  70                  75                  80

Gln Gly Leu Arg Gly Ser Asn Ser Cys Asp Glu Glu Leu Gly Ala Phe
                 85                  90                  95

Ile Gly Asp Ser Ser Met His Ser Thr Glu Val Gln His Tyr His Val
            100                 105                 110

Tyr Asp His Ser Gly Glu Lys Val Glu Gly Val Glu Asp Ala Asp Ser
        115                 120                 125

Ile Leu Val Gln Ser Gly Ala Asp Asp Gly Val Glu Val Trp Gly Gly
    130                 135                 140

Asp Glu Glu Ser Glu Asn Ser Asp Val Asp Ser Gly Glu Pro Asp Pro
145                 150                 155                 160

Glu Gly Ser Ala Pro Ala Asp Trp Gly Ser Ser Pro Ile Ser Pro Ala
                165                 170                 175

Thr Arg Ala Ser Asp Val Glu Thr Val Glu Gly Asp Glu Ile Gln Lys
            180                 185                 190

Leu Leu Glu Asp Gln Ser Arg Ile Arg Lys Met Thr Lys Ala Glu Lys
        195                 200                 205

Thr Leu Val Val Pro Pro Ile Pro Ser Gln Glu Arg Pro Thr Ala Ser
    210                 215                 220

Glu Lys Pro Ile Lys Lys Gly His Arg Arg Glu Ile Asp Leu Ile Trp
225                 230                 235                 240

Asn Asp Gly Arg Val Phe Ile Asp Arg Trp Cys Asn Pro Thr Cys Ser
                245                 250                 255

Lys Val Thr Val Gly Thr Val Arg Ala Lys Cys Ile Cys Gly Glu Cys
            260                 265                 270

Pro Arg Val Cys Glu Gln Cys Ile Thr Asp Ser Gly Ile Glu Asn Arg
        275                 280                 285

Ile Trp Tyr His Asn Leu Ala Asp Ile Pro Glu
    290                 295

<210> SEQ ID NO 3
<211> LENGTH: 303
<212> TYPE: PRT
<213> ORGANISM: Dolphin morbillivirus

<400> SEQUENCE: 3

Met Ala Glu Glu Gln Ala Tyr His Ile Asn Lys Gly Leu Glu Cys Leu
  1               5                  10                  15

Lys Ser Leu Arg Glu Asn Pro Pro Asp Ala Val Glu Ile Lys Glu Ala
             20                  25                  30

Gln Ile Ile Arg Ser Lys Ala Ala Cys Glu Glu Ser Ser Glu Ser His
         35                  40                  45

His Gln Asp Asn Ser Glu Lys Asp Thr Leu Asp Phe Asp Glu Ser Cys
     50                  55                  60

Ser Ser Ala Ile Arg Pro Glu Thr Tyr Arg Met Leu Leu Gly Asp Asp
 65                  70                  75                  80

Thr Gly Phe Arg Ala Pro Gly Tyr Ile Pro Asn Glu Gly Glu Pro Glu
                 85                  90                  95
```

```
Pro Gly Asp Ile Gly Lys Glu Glu Pro Ala Val Arg Cys Tyr His Val
            100                 105                 110

Tyr Asp His Gly Gly Gln Ala Val Glu Gly Val Lys Asp Ala Asp Leu
        115                 120                 125

Leu Val Val Pro Thr Gly Ser Asp Asp Ala Glu Phe Arg Asp Gly
    130                 135                 140

Asp Glu Ser Ser Leu Glu Ser Asp Gly Glu Ser Gly Thr Val Asp Thr
145                 150                 155                 160

Arg Gly Asn Ser Ser Asn Arg Gly Ser Ala Pro Arg Ile Lys Val
                165                 170                 175

Glu Arg Ser Ser Asp Val Glu Thr Ile Ser Ser Glu Glu Leu Gln Gly
            180                 185                 190

Leu Ile Arg Ser Gln Ser Gln Lys His Asn Gly Phe Gly Val Asp Arg
        195                 200                 205

Phe Leu Lys Val Pro Pro Ile Pro Thr Ser Val Pro Leu Asp Pro Ala
    210                 215                 220

Pro Lys Ser Ile Lys Lys Gly His Arg Arg Glu Ile Ser Leu Ile Trp
225                 230                 235                 240

Asp Gly Asp Arg Val Phe Ile Asp Arg Trp Cys Asn Pro Thr Cys Ser
                245                 250                 255

Arg Ile Lys Met Gly Ile Val Arg Val Lys Cys Thr Cys Gly Glu Cys
            260                 265                 270

Pro Pro Val Cys Asp Glu Cys Arg Glu Asp Pro Glu Thr Pro Thr Arg
        275                 280                 285

Ile Trp Tyr His Ser Leu Pro Glu Ile Pro Glu Gln Trp Pro Phe
    290                 295                 300

<210> SEQ ID NO 4
<211> LENGTH: 299
<212> TYPE: PRT
<213> ORGANISM: canine distemper virus

<400> SEQUENCE: 4

Met Ala Glu Glu Gln Ala Tyr His Val Ser Lys Gly Leu Glu Cys Leu
  1               5                  10                  15

Lys Ala Leu Arg Glu Asn Pro Pro Asp Ile Glu Glu Ile Gln Glu Val
             20                  25                  30

Ser Ser Leu Arg Asp Gln Thr Cys Asn Pro Gly Gln Glu Asn Gly Thr
         35                  40                  45

Thr Gly Met Gln Glu Glu Asp Ser Gln Asn Leu Asp Glu Ser His
     50                  55                  60

Glu Pro Thr Lys Gly Ser Asn Tyr Val Gly His Val Pro Gln Asn Asn
 65                  70                  75                  80

Pro Gly Cys Gly Glu Arg Asn Thr Ala Leu Val Glu Ala Glu Arg Pro
                 85                  90                  95

Pro Arg Glu Asp Ile Gln Pro Gly Pro Gly Ile Arg Cys Asp His Val
            100                 105                 110

Tyr Asp His Ser Gly Glu Glu Val Lys Gly Ile Glu Asp Ala Asp Ser
        115                 120                 125

Leu Val Val Pro Ala Gly Thr Val Gly Asn Arg Gly Phe Glu Arg Gly
    130                 135                 140

Glu Gly Ser Leu Asp Asp Ser Thr Glu Asp Ser Gly Glu Asp Tyr Ser
145                 150                 155                 160

Glu Gly Asn Ala Ser Ser Asn Trp Gly Tyr Ser Phe Gly Leu Lys Pro
                165                 170                 175
```

-continued

Asp Arg Ala Ala Asp Val Ser Met Leu Met Glu Glu Leu Ser Ala
        180                 185                 190

Leu Le

Gln Ser Gly Leu Asp Gly Asp Ser Thr
        35                  40

<210> SEQ ID NO 9
<211> LENGTH: 18
<212> TYPE: PRT
<213> ORGANISM: Measles virus

<400> SEQUENCE: 9

Leu Gln Ala Ser Ser Thr Gly Leu Gln Cys Tyr Tyr Leu Asp Gly Asp
 1               5                  10                  15

Ser Thr

<210> SEQ ID NO 10
<211> LENGTH: 41
<212> TYPE: PRT
<213> ORGANISM: Measles virus

<400> SEQUENCE: 10

Leu Gln Ala Ser Ser Thr Gly Leu Gln Cys Tyr Tyr Val Tyr Ala Ala
 1               5                  10                  15

Ser Gly Glu Ala Val Lys Gly Ile Gln Asp Ala Asp Ser Ile Met Val
            20                  25                  30

Gln Ser Gly Leu Asp Gly Asp Ser Thr
        35                  40

<210> SEQ ID NO 11
<211> LENGTH: 41
<212> TYPE: PRT
<213> ORGANISM: Measles virus

<400> SEQUENCE: 11

Leu Gln Ala Ser Ser Thr Gly Leu Gln Cys Tyr Tyr Val Ala Ala Ala
 1               5                  10                  15

Ser Gly Glu Ala Val Lys Gly Ile Gln Asp Ala Asp Ser Ile Met Val
            20                  25                  30

Gln Ser Gly Leu Asp Gly Asp Ser Thr
        35                  40

<210> SEQ ID NO 12
<211> LENGTH: 80
<212> TYPE: PRT
<213> ORGANISM: Measles virus

<400> SEQUENCE: 12

Arg Ala Ser Thr Ser Glu Thr Pro Ile Lys Lys Gly His Arg Arg Glu
 1               5                  10                  15

Ile Ser Leu Ile Trp Asn Gly Asp Arg Val Phe Ile Asp Arg Trp Cys
            20                  25                  30

Asn Pro Met Cys Ser Lys Val Thr Leu Gly Thr Ile Arg Ala Arg Cys
        35                  40                  45

Thr Cys Gly Glu Cys Pro Arg Val Cys Glu Gln Cys Arg Thr Asp Thr
    50                  55                  60

Gly Val Asp Thr Arg Ile Trp Tyr His Asn Leu Pro Glu Ile Pro Glu
65                  70                  75                  80

<210> SEQ ID NO 13
<211> LENGTH: 12
<212> TYPE: PRT
<213> ORGANISM: Measles virus

```
<400> SEQUENCE: 13

Arg Ala Ser Thr Ser Glu Thr Pro Ile Lys Lys Gly
1               5                   10

<210> SEQ ID NO 14
<211> LENGTH: 80
<212> TYPE: PRT
<213> ORGANISM: Measles virus

<400> SEQUENCE: 14

Arg Ala Ser Thr Ser Glu Thr Pro Ile Lys Lys Gly His Arg Arg Glu
1               5                   10                  15

Ile Ser Leu Ile Trp Asn Gly Asp Arg Val Phe Ile Asp Arg Trp Ala
            20                  25                  30

Asn Pro Met Ala Ser Lys Val Thr Leu Gly Thr Ile Arg Ala Arg Cys
        35                  40                  45

Thr Cys Gly Glu Cys Pro Arg Val Cys Glu Gln Cys Arg Thr Asp Thr
    50                  55                  60

Gly Val Asp Thr Arg Ile Trp Tyr His Asn Leu Pro Glu Ile Pro Glu
65                  70                  75                  80

<210> SEQ ID NO 15
<211> LENGTH: 80
<212> TYPE: PRT
<213> ORGANISM: Measles virus

<400> SEQUENCE: 15

Arg Ala Ser Thr Ser Glu Thr Pro Ile Lys Lys Gly His Arg Arg Glu
1               5                   10                  15

Ile Ser Leu Ile Trp Asn Gly Asp Arg Val Phe Ile Asp Arg Trp Cys
            20                  25                  30

Asn Pro Met Cys Ser Lys Val Thr Leu Gly Thr Ile Arg Ala Arg Cys
        35                  40                  45

Thr Ala Gly Glu Ala Pro Arg Val Cys Glu Gln Cys Arg Thr Asp Thr
    50                  55                  60

Gly Val Asp Thr Arg Ile Trp Tyr His Asn Leu Pro Glu Ile Pro Glu
65                  70                  75                  80

<210> SEQ ID NO 16
<211> LENGTH: 59
<212> TYPE: PRT
<213> ORGANISM: Measles virus

<400> SEQUENCE: 16

Arg Ala Ser Thr Ser Glu Thr Pro Ile Lys Lys Gly His Arg Arg Glu
1               5                   10                  15

Ile Ser Leu Ile Trp Asn Gly Asp Arg Val Phe Ile Asp Arg Trp Cys
            20                  25                  30

Asn Pro Met Cys Ser Lys Val Thr Leu Gly Thr Ile Arg Ala Arg Cys
        35                  40                  45

Thr Cys Gly Glu Cys Pro Arg Val Cys Glu Gln
    50                  55

<210> SEQ ID NO 17
<211> LENGTH: 47
<212> TYPE: PRT
<213> ORGANISM: Measles virus
```

```
<400> SEQUENCE: 17

Arg Ala Ser Thr Ser Glu Thr Pro Ile Lys Lys Gly His Arg Arg Glu
 1               5                  10                  15

Ile Ser Leu Ile Trp Asn Gly Asp Arg Val Phe Ile Asp Arg Trp Cys
            20                  25                  30

Asn Pro Met Cys Ser Lys Val Thr Leu Gly Thr Ile Arg Ala Arg
        35                  40                  45

<210> SEQ ID NO 18
<211> LENGTH: 30
<212> TYPE: PRT
<213> ORGANISM: Measles virus

<400> SEQUENCE: 18

Arg Ala Ser Thr Ser Glu Thr Pro Ile Lys Lys Gly His Arg Arg Glu
 1               5                  10                  15

Ile Ser Leu Ile Trp Asn Gly Asp Arg Val Phe Ile Asp Arg
            20                  25                  30

<210> SEQ ID NO 19
<211> LENGTH: 23
<212> TYPE: PRT
<213> ORGANISM: Measles virus

<400> SEQUENCE: 19

Arg Ala Ser Thr Ser Glu Thr Pro Ile Lys Lys Gly His Arg Arg Glu
 1               5                  10                  15

Ile Ser Leu Ile Trp Asn Gly
            20

<210> SEQ ID NO 20
<211> LENGTH: 16
<212> TYPE: PRT
<213> ORGANISM: Measles virus

<400> SEQUENCE: 20

Arg Ala Ser Thr Ser Glu Thr Pro Ile Lys Lys Gly His Arg Arg Glu
 1               5                  10                  15

<210> SEQ ID NO 21
<211> LENGTH: 9
<212> TYPE: PRT
<213> ORGANISM: Measles virus

<400> SEQUENCE: 21

Arg Ala Ser Thr Ser Glu Thr Pro Ile
 1               5

<210> SEQ ID NO 22
<211> LENGTH: 80
<212> TYPE: PRT
<213> ORGANISM: Measles virus

<400> SEQUENCE: 22

Arg Ala Ser Thr Ser Glu Thr Pro Ile Lys Lys Gly His Ala Ala Glu
 1               5                  10                  15

Ile Ser Leu Ile Trp Asn Gly Asp Arg Val Phe Ile Asp Arg Trp Cys
            20                  25                  30

Asn Pro Met Cys Ser Lys Val Thr Leu Gly Thr Ile Arg Ala Arg Cys
        35                  40                  45
```

-continued

```
Thr Cys Gly Glu Cys Pro Arg Val Cys Glu Gln Cys Arg Thr Asp Thr
         50                  55                  60

Gly Val Asp Thr Arg Ile Trp Tyr His Asn Leu Pro Glu Ile Pro Glu
 65                  70                  75                  80

<210> SEQ ID NO 23
<211> LENGTH: 80
<212> TYPE: PRT
<213> ORGANISM: Measles virus

<400> SEQUENCE: 23

Arg Ala Ser Thr Ser Glu Thr Pro Ile Lys Lys Gly His Asp Asp Glu
 1               5                  10                  15

Ile Ser Leu Ile Trp Asn Gly Asp Arg Val Phe Ile Asp Arg Trp Cys
             20                  25                  30

Asn Pro Met Cys Ser Lys Val Thr Leu Gly Thr Ile Arg Ala Arg Cys
         35                  40                  45

Thr Cys Gly Glu Cys Pro Arg Val Cys Glu Gln Cys Arg Thr Asp Thr
     50                  55                  60

Gly Val Asp Thr Arg Ile Trp Tyr His Asn Leu Pro Glu Ile Pro Glu
 65                  70                  75                  80

<210> SEQ ID NO 24
<211> LENGTH: 71
<212> TYPE: PRT
<213> ORGANISM: Measles virus

<400> SEQUENCE: 24

Arg Ala Ser Thr Ser Glu Thr Pro Ile Leu Ile Trp Asn Gly Asp Arg
 1               5                  10                  15

Val Phe Ile Asp Arg Trp Cys Asn Pro Met Cys Ser Lys Val Thr Leu
             20                  25                  30

Gly Thr Ile Arg Ala Arg Cys Thr Cys Gly Glu Cys Pro Arg Val Cys
         35                  40                  45

Glu Gln Cys Arg Thr Asp Thr Gly Val Asp Thr Arg Ile Trp Tyr His
     50                  55                  60

Asn Leu Pro Glu Ile Pro Glu
 65                  70
```

MODIFIED MORBILLIVIRUS V PROTEINS

This application claims the benefit of provisional application No. 60/213,655, filed Jun. 23, 2000.

FIELD OF THE INVENTION

This invention relates to isolated, recombinantly-generated, negative-sense, single-stranded RNA viruses of the genus Morbillivirus having one or more mutations and/or deletions which reduce the repression normally caused by the V protein.

BACKGROUND OF THE INVENTION

Enveloped, negative-sense, single-stranded RNA viruses are uniquely organized and expressed. The genomic RNA of negative-sense, single-stranded viruses serves two template functions in the context of a nucleocapsid: as a template for the synthesis of messenger RNAs (mRNAs) and as a template for the synthesis of the antigenome (+) strand. Viral replication occurs after synthesis of the mRNAs and requires the continuous synthesis of viral proteins. The newly synthesized antigenome (+) strand serves as the template for generating further copies of the (−) strand genomic RNA.

The RNA-dependent RNA polymerase complex actuates and achieves transcription and replication by engaging the cis-acting signals at the 3' end of the genome, in particular, the promoter region. Viral genes are then transcribed from the genome template unidirectionally from its 3' to its 5' end.

Based on the revised reclassification in 1993 by the International Committee on the Taxonomy of Viruses, an Order, designated Mononegavirales, has been established. This Order contains three families of enveloped viruses with single-stranded, nonsegmented RNA genomes of minus polarity (negative-sense). These families are the Paramyxoviridae, Rhabdoviridae and Filoviridae. The family Paramyxoviridae has been further divided into two subfamilies, Paramyxovirinae and Pneumovirinae. The subfamily Paramyxovirinae contains three genera, Respirovirus (formerly Paramyxovirus), Rubulavirus and Morbillivirus. The subfamily Pneumovirinae contains the genus Pneumovirus. The new classification is based upon morphological criteria, the organization of the viral genome, biological activities and the sequence relatedness of the genes and gene products. The current taxonomical classification of the Morbilliviruses is as follows:

Order Mononegavirales
   Family Paramyxoviridae
      Subfamily Paramyxovirinae
         Genus Morbillivirus
            Measles virus
            Dolphin morbillivirus
            Canine distemper virus
            Peste-des-petits-ruminants virus
            Phocine distemper virus
            Rinderpest virus For many of these viruses, no vaccines of any kind are available. Thus, there is a need to develop vaccines against such human and animal pathogens. Such vaccines would have to elicit a protective immune response in the recipient. The qualitative and quantitative features of such a favorable response are extrapolated from those seen in survivors of natural virus infection, who, in general, are protected from reinfection by the same or highly related viruses for some significant duration thereafter.

A variety of approaches can be considered in seeking to develop such vaccines, including the use of: (1) purified individual viral protein vaccines (subunit vaccines); (2) inactivated whole virus preparations; and (3) live, attenuated viruses.

Subunit vaccines have the desirable feature of being pure, definable and relatively easily produced in abundance by various means, including recombinant DNA expression methods. To date, with the notable exception of hepatitis B surface antigen, viral subunit vaccines have generally only elicited short-lived and/or inadequate immunity, particularly in naive recipients.

Formalin inactivated whole virus preparations of polio (IPV) and hepatitis A have proven safe and efficacious. In contrast, immunization with similarly inactivated whole viruses such as respiratory syncytial virus and measles virus vaccines elicited unfavorable immune responses and/or response profiles which predisposed vaccinees to exaggerated or aberrant disease when subsequently confronted with the natural or "wild-type" virus.

Appropriately attenuated live derivatives of wild-type viruses offer a distinct advantage as vaccine candidates. As live, replicating agents, they initiate infection in recipients during which viral gene products are expressed, processed and presented in the context of the vaccinee's specific MHC class I and II molecules, eliciting humoral and cell-mediated immune responses, as well as the coordinate cytokine and chemokine patterns, which parallel the protective immune profile of survivors of natural infection.

This favorable immune response pattern is contrasted with the delimited responses elicited by inactivated or subunit vaccines, which typically are largely restricted to the humoral immune surveillance arm. Further, the immune response profile elicited by some formalin inactivated whole virus vaccines, e.g., measles and respiratory syncytial virus vaccines developed in the 1960's, have not only failed to provide sustained protection, but in fact have led to a predisposition to aberrant, exaggerated, and even fatal illness, when the vaccine recipient later confronted the wild-type virus.

While live, attenuated viruses have highly desirable characteristics as vaccine candidates, they have proven to be difficult to develop. The crux of the difficulty lies in the need to isolate a derivative of the wild-type virus which has lost its disease-producing potential (i.e., virulence), while retaining sufficient replication competence to infect the recipient and elicit the desired immune response profile in adequate abundance.

Historically, this delicate balance between virulence and attenuation has been achieved by serial passage of a wild-type viral isolate through different host tissues or cells under varying growth conditions (such as temperature). This process presumably favors the growth of viral variants (mutants), some of which have the favorable characteristic of attenuation. Occasionally, further attenuation is achieved through chemical mutagenesis as well.

This propagation/passage scheme typically leads to the emergence of virus derivatives which are temperature sensitive, cold-adapted and/or altered in their host range—one or all of which are changes from the wild-type, disease-causing viruses—i.e., changes that may be associated with attenuation.

Several live virus vaccines, including those for the prevention of measles and mumps (which are paramyxoviruses), and for protection against polio and rubella (which are positive strand RNA viruses), have been generated by this approach and provide the mainstay of current childhood immunization regimens throughout the world.

Nevertheless, this means for generating attenuated live virus vaccine candidates is lengthy and, at best, unpredictable, relying largely on the selective outgrowth of those randomly occurring genomic mutants with desirable attenuation characteristics. The resulting viruses may have the desired phenotype in vitro, and even appear to be attenuated in animal models. However, all too often they remain either under- or overattenuated in the human or animal host for whom they are intended as vaccine candidates.

Even as to current vaccines in use, there is still a need for more efficacious vaccines. For example, the current measles vaccines provide reasonably good protection. However, recent measles epidemics suggest deficiencies in the efficacy of current vaccines. Despite maternal immunization, high rates of acute measles infection have occurred in children under age one, reflecting the vaccines, inability to induce anti-measles antibody levels comparable to those developed following wild-type measles infection (Bibliography entries 1,2,3). As a result, vaccine-immunized mothers are less able to provide their infants with sufficient transplacentally-derived passive antibodies to protect the newborns beyond the first few months of life.

Acute measles infections in previously immunized adolescents and young adults point to an additional problem. These secondary vaccine failures indicate limitations in the current vaccines' ability to induce and maintain antiviral protection that is both abundant and long-lived (4,5,6). Recently, yet another potential problem was revealed. The hemagglutinin protein of wild-type measles isolated over the past 15 years has shown a progressively increasing distance from the vaccine strains (7). This "antigenic drift" raises legitimate concerns that the vaccine strains may not contain the ideal antigenic repertoire needed to provide optimal protection. Thus, there is a need for improved vaccines.

Rational vaccine design would be assisted by a better understanding of these viruses, in particular, by the identification of the virally encoded determinants of virulence as well as those genomic changes which are responsible for attenuation.

Because of its significance as a major cause of human morbidity and mortality, measles virus has been quite extensively studied. Measles virus is a large, relatively spherical, enveloped particle composed of two compartments, a lipoprotein membrane and a ribonucleoprotein particle core, each having distinct biological functions (8). The virion envelope is a host cell-derived plasma membrane modified by three virus-specified proteins: The hemagglutinin (H; approximately 80 kilodaltons (kD)) and fusion ($F_{1,2}$; approximately 60 kD) glycoproteins project on the virion surface and confer host cell attachment and entry capacities to the viral particle (9). Antibodies to H and/or F are considered protective since they neutralize the virus' ability to initiate infection (10,11,12). The matrix (M; approximately 37 kD) protein is the amphipathic protein lining the membrane's inner surface, which is thought to orchestrate virion morphogenesis and thus consuxmate virus reproduction (13). The virion core contains the 15,894 nucleotide long genomic RNA upon which template activity is conferred by its intimate association with approximately 2600 molecules of the approximately 60 kD nucleocapsid (N) protein (14,15,16). Loosely associated with this approximately one micron long helical ribonucleoprotein particle are enzymatic levels of the viral RNA-dependent RNA polymerase (L; approximately 240 kD) which in concert with the polymerase cofactor (P; approximately 70 kD), and perhaps yet other virus-specified as well as host-encoded proteins, transcribes and replicates the measles virus genome sequences (17).

The six virion structural proteins of measles virus are encoded by six contiguous, non-overlapping genes which are arrayed as follows: 3'-N-P-M-F-H-L-5'. Two additional measles virus gene products of as yet uncertain function have also been identified. These two nonstructural proteins, known as C (approximately 20 kD) and V (approximately 45 kD), are both encoded by the P gene. The C protein is encoded by a second reading frame within the P mRNA. The V protein is encoded by a cotranscriptionally edited P gene-derived mRNA which encodes a hybrid protein having the amino terminal sequences of P and a zinc finger-like cysteine-rich carboxy terminal domain which is lacking in the P protein (9).

All Morbilliviruses produce a V protein (18), including measles virus, rinderpest virus, canine distemper virus and phocine distemper virus (19). Measles virus V protein is a nonstructural protein encoded by the P gene (8). Like most paramyxoviruses, measles virus encodes multiple proteins from the P gene including V protein, P protein, and C protein (9). Translation of both P and V proteins initiates at the same methionine codon resulting in polypeptides that are identical for the first 230 amino acids. The carboxy-terminus (C-terminus) of V protein differs from P protein because RNA editing occurs in some P gene mRNAs causing a frameshift that results in translation of a shorter, unique V protein C-terminus (18). The C protein amino acid sequence is unrelated to V and P protein because it is translated entirely from a different reading frame that begins at a downstream translation initiation codon (20).

The P and V mRNAs of measles virus share the same start codon and the first 230 amino acids of the P and V proteins are identical. The V mRNA contains a "G" residue insertion that expands the sequence "GGG" at nucleotides 2496 to 2498 to include a fourth "G" residue. Editing takes place during transcription when an extra non-template-directed "G" residue is inserted between nucleotides 2495 and 2499, causing a shift in the reading frame, whereby the carboxy-terminal 276 amino acids of the P protein are replaced with a 68 amino acid cysteine-rich carboxy-terminus of the V protein.

The function of V protein is not well understood, but all Morbilliviruses encode a V protein. This indicates that V protein performs beneficial functions that have made it advantageous for Morbilliviruses to conserve the capacity to synthesize V protein. It is known that V protein expression is not essential for viral replication in cultured cells (19, 21–25), but in animal model systems expression of V protein seems to influence the severity of infection. For example, Sendai virus (a non-Morbillivirus paramyxovirus) normally produces pneumonia in mouse model systems but is less virulent if the infection is performed with a recombinant virus that is defective for V protein expression (22,26). Recombinant human parainfluenza virus type 3 (another non-Morbillivirus paramyxovirus) also exhibits an attenuated phenotype in rodents and monkeys if a defect in D protein expression is combined with a defect in the V protein open reading frame (23).

Similarly, results from studies with animal model systems used for measles virus also suggest a role for V protein in pathogenicity. Infection of cotton rat lungs by recombinant measles virus generates less progeny virus if the infecting virus was defective for V protein expression (27). Also, human thymocyte survival in tissue transplanted in SCID mice was less susceptible to infection with measles virus if the infecting virus did not express V protein (28). Finally, CD46 transgenic mice inoculated intracranially with measles virus had greater rates of survival if the virus did not express V protein (29). The conclusion that measles virus V protein plays a role in pathogenicity also is supported by sequence analyses that have found V protein coding region mutations in less pathogenic variants or vaccine strains (30,31). Taken together, these results support the hypothesis that V protein plays an important role in determining the virulence of measles virus and several other paramyxoviruses.

Although it seems clear that V protein can influence the course of infection, the mechanism behind this phenomenon is not known. Results from a number of studies have begun to assign potential functions to V protein. For example, it has been shown that amino acid sequences shared by V protein and P protein mediate interaction with the viral nucleocapsid (N) protein (27,32–39). This interaction between V protein and N protein seems to affect the cellular distribution N protein (27,40,41) and probably has some additional unidentified functions. Some V proteins also have been found to interact with cellular proteins (42,43), and in the case of simian virus 5 (SV5), it is possible that interaction with a cellular protein is responsible for inhibition of the interferon signaling pathway during infection (44). In addition to the protein-protein interactions-that involve V protein, several studies have linked V protein to control mechanisms that regulate viral gene expression and replication. Sendai virus V protein expression in a transient expression system inhibits defective-interfering (DI) particle replication (45) and similarly inhibits DI particle replication in an in vitro transcription reaction (35). Consistent with these observations relating V protein with repression, several viruses defective for V protein expression have been observed to produce elevated levels of genome RNA, mRNA, and viral proteins during infection (21,26,27).

In addition to the properties just described, all of the viral V proteins contain a cysteine-rich C-terminus. The paramyxovirus V proteins do not share a high degree of amino acid similarity, but they all contain seven identically positioned cysteine residues (46). This striking feature has led to speculation (47) that V proteins may actually be zinc-finger proteins or at least form some type of zinc-coordinated secondary structure (48,49,50), and in fact, several V proteins have been found to bind zinc (51,52,53). The possibility that V protein forms a zinc-coordinated structure generates considerable interest because these types of structures often form protein domains that are involved in nucleic acid interaction or protein-protein interaction (48,49,50). It is also noteworthy that a recombinant Sendai virus that expresses a truncated V protein lacking the unique C-terminal region also is less pathogenic, suggesting that the role of V protein in pathogenicity requires this domain (24).

In addition to the sequences encoding the virus-specified proteins, the measles virus genome contains distinctive non-protein coding domains resembling those directing the transcriptional and replicative pathways of related viruses (9,54). These regulatory signals lie at the 3' and 5' ends of the measles virus genome and in short internal regions spanning each intercistronic boundary. The former encode the putative promoter and/or regulatory sequence elements directing genomic transcription, genome and antigenome encapsidation, and replication. The latter signal transcription termination and polyadenylation of each monocistronic viral mRNA and then reinitiation of transcription of the next gene. In general, the measles virus polymerase complex appears to respond to these signals much as the RNA-dependent RNA polymerases of other non-segmented negative strand RNA viruses (9,54,55,56). Transcription initiates at or near the 3' end of the measles virus genome and then proceeds in a 5' direction-producing monocistronic mRNAs (16,54,57).

Measles virus appears to have extended its terminal regulatory domains beyond the confines of leader and trailer encoding sequences (54). For measles, these regions encompass the 107 3' genomic nucleotides (the "3' genomic promoter region", also referred to as the "extended promoter", which comprises 52 nucleotides encoding the leader region, followed by three intergenic nucleotides, and 52 nucleotides encoding the 5' untranslated region of N mRNA) and the 109 5' end nucleotides (69 encoding the 3' untranslated region of L mRNA, the intergenic trinucleotide and 37 nucleotides encoding the trailer). Within these 3' terminal approximately 100 nucleotides of both the genome and antigenome are two short regions of shared nucleotide sequence: 14 of 16 nucleotides at the absolute 3' ends of the genome and antigenome are identical. Internal to those termini, an additional region of 12 nucleotides of absolute sequence identity have been located. Their position at and near the sites at which the transcription of the measles virus genome must initiate and replication of the antigenome must begin, suggests that these short unique sequence domains encompass an extended promoter region.

These discrete sequence elements may dictate alternative sites of transcription initiation—the internal domain mandating transcription initiation at the N gene start site, and the 3' terminal domain directing antigenome production (54,58, 59). In addition to their regulatory role as cis-acting determinants of transcription and replication, these 3' extended genomic and antigenomic promoter regions encode the nascent 5' ends of antigenome and genome RNAs, respectively. Within these nascent RNAs reside as yet unidentified signals for N protein nucleation, another key regulatory element required for nucleocapsid template formation and consequently for amplification of transcription and replication.

In all Morbilliviruses, the cis-acting signals required for essential viral functions, including replication, transcription and encapsidation are contained in the non-coding genomic termini. The obligatory trans-acting elements for functionality are contained in the N, P and L genes. Additional transacting factors, such as the V and C proteins, may modulate functionality. Mutations in any of these regions may result in alteration of vital functions, including attenuation of viral transcription/-replication efficiency.

The apparent connection between V protein expression and pathogenicity, and continuing interest in vaccine attenuation (30,60) has led to a need to examine measles virus V protein function in more detail. In particular, there is a need to utilize transient expression systems to study several V protein properties including V protein repression activity, the interaction of V protein with N protein, and the ability of V protein to bind RNA.

SUMMARY OF THE INVENTION

Accordingly, it is an object of this invention to identify regions of the genomes of Morbilliviruses responsible for the repression of gene expression by the V protein of those viruses. It is a further object of this invention to generate mutant versions of the V protein of Morbilliviruses in which the repression of gene expression is reduced. It is a still further object of this invention to generate recombinantly-generated Morbilliviruses containing one or more of such mutations. It is yet another object of this invention to formulate vaccines or immunogenic compositions containing such recombinantly-generated Morbilliviruses. In one embodiment of the invention, the V protein is from measles virus.

These and other objects of the invention as discussed below are achieved for Morbilliviruses by modifying the region corresponding to amino acids 112–134 (conserved region 2; see FIG. 2) of the V protein of these Morbilliviruses, wherein one or both of amino acids 113 (a tyrosine) and 114 (asparatic acid) is mutated. In one embodiment of the invention, these amino acids are mutated to alanine.

A further modification of the V protein may be made by mutating or deleting at least a portion of the carboxy-terminal (C-terminal) region of the Morbillivirus V protein, corresponding to amino acids 231–299 of the V protein of measles virus, canine distemper virus and dolphin morbillivirus, and to amino acids 231–303 of the rinderperst virus.

These modifications have the effect of reducing the repression of gene expression by the V protein in a minireplicon system. The results are extended readily to the recovery of full-length infectious Morbilliviruses by the use of the "rescue" system known in the art and described below.

Measles virus minireplicon with chloramphenicol acetyltransferase (CAT) reporter gene expression in transient assays was strongly repressed by V protein. Repression activity was diminished by amino acid substitution in a region located in the amino terminal third of the protein between amino acids 112–134, as well as by mutating or deleting at least a portion of the cysteine-rich C-terminal region of V protein (amino acids 231–299).

In the case of measles virus, the mutations described above may be further combined with mutations which are attenuating, as follows:

(1) at least one attenuating mutation in the 3' genomic promoter region selected from the group consisting of nucleotide 26 (A→T), nucleotide 42 (A→T or A→C) and nucleotide 96 (G→A), where these nucleotides are presented in positive strand, antigenomic, message sense;

(2) at least one attenuating mutation in the RNA polymerase gene selected from the group consisting of nucleotide changes which produce changes in an amino acid selected from the group consisting of residues 331 (isoleucine→threonine), 1409 (alanine→threonine), 1624 (threonine→alanine), 1649 (arginine→methionine), 1717 (aspartic acid→alanine), 1936 (histidine→tyrosine), 2074 (glutamine→arginine) and 2114 (arginine→lysine);

(3) for the N gene, at least one attenuating mutation selected from the group consisting of nucleotide changes which produce changes in an amino acid selected from the group consisting of residues 129 (glutamine→lysine), 148 (glutamic acid→glycine) and 479 (serine→threonine);

(4) for the P gene, at least one attenuating mutation selected from the group consisting of nucleotide changes which produce changes in an amino acid selected from the group consisting of residues 225 (glutamic acid→glycine), 275 (cysteine→tyrosine) and 439 (leucine→proline);

(5) for the C gene, at least one attenuating mutation selected from the group consisting of nucleotide changes which produce changes in an amino acid selected from the group consisting of residues 73 (alanine→valine), 104 (methionine→threonine) and 134 (serine→tyrosine); and (6) for the F gene-end signal (the cis-acting transcription termination signal), the change at nucleotide 7243 (T→C), where these nucleotides are presented in positive strand, antigenomic, that is, message (coding) sense.

In another embodiment of this invention, these mutant Morbilliviruses are used to prepare vaccines or immunogenic compositions which elicit a protective immune response against the wild-type form of each virus.

In a further embodiment of this invention, there is described a method for reducing the repression caused by a V protein of Morbilliviruses which comprises inserting at least one mutation in the region corresponding to amino acids 112–134 of a Morbillivirus V protein, wherein the mutation in the region corresponding to amino acids 112–134 of a Morbillivirus V protein is selected from the group consisting of the mutation of amino acids 113 and 114.

In still another embodiment of this invention, there is described an isolated nucleotide sequence encoding a Morbilliviruses V protein which has been modified by inserting at least one mutation in the region corresponding to amino acids 112–134 of a Morbillivirus V protein, wherein the mutation in the region corresponding to amino acids 112–134 of a Morbillivirus V protein is selected from the group consisting of the mutation of amino acids 113 and 114.

In yet another embodiment of this invention, there is provided a composition which comprises a transcription vector comprising an isolated nucleic acid molecule encoding a genome or antigenome of a Morbillivirus, wherein the portion of the isolated nucleic acid molecule encoding the V protein has been modified so as to insert at least one mutation in the region corresponding to amino acids 112–134 of a Morbillivirus V protein, wherein the mutation in the region corresponding to amino acids 112–134 of a Morbillivirus V protein is selected from the group consisting of the mutation of amino acids 113 and 114, together with at least one expression vector which comprises at least one isolated nucleic acid molecule encoding the trans-acting proteins N, P and L necessary for encapsidation, transcription and replication, whereby host cells are transformed, infected or transfected with these vectors and cultured under conditions which permit the co-expression of these vectors so as to produce the desired Morbillivirus. Each such virus is then used to prepare vaccines or immunogenic compositions which elicit a protective immune response against the wild-type form of each virus.

BRIEF DESCRIPTION OF THE FIGURES

FIG. 2 depicts a comparison of the amino acid sequences of V proteins from four different Morbilliviruses. Edmonston wild-type measles virus V protein amino acid sequence (Gene Bank accession number AF266288)(SEQ ID NO:1) was compared to canine distemper virus (AF014953)(SEQ ID NO:4), rinderpest virus (Z30697)(SEQ ID NO:2), and dolphin morbillivirus (Z47758)(SEQ ID NO:3). Regions containing higher levels of identity are overlined with a cross-hatched bar and designated as conserved regions (CR1 through CR6). Additional notable sequences are underlined with a black bar. These include regions involved in the V (and P) protein interaction with N protein (34), a region involved in the cellular localization of the V-N protein complex (27,64), and the cysteine-rich region that contains the zinc-binding domain (51). Other sequences of interest include a basic region between 229–234, a measles virus vaccine amino acid substition (glutamic acid to glycine) at position 225 (30), and a leucine repeat region reminiscent of a leucine zipper between positions 93–107 (65,66). The region common to V and P protein extends from amino acid 1–230 and the unique V protein sequences (bold amino acid letters) extend from 231–299. The amino acid positions given in the Figure along the top of the aligned sequences correspond to those of the measles virus V protein.

DETAILED DESCRIPTION OF THE INVENTION

Figure 1A:
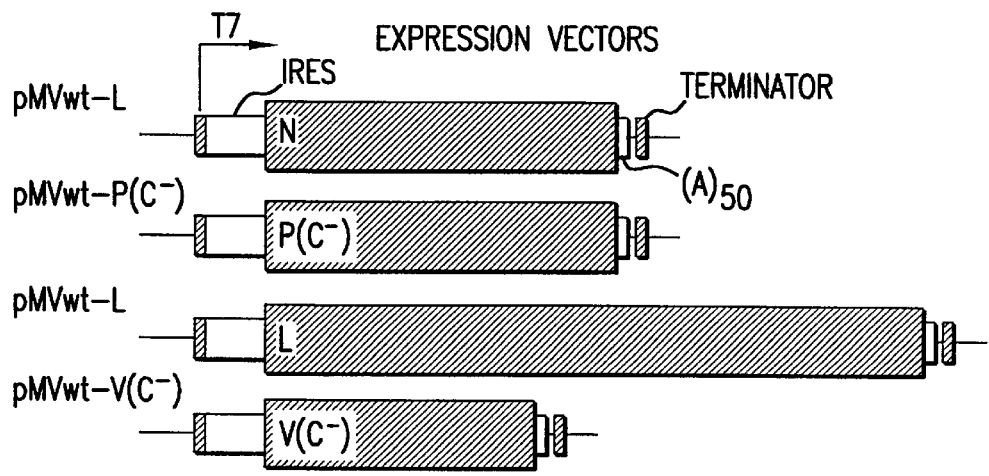
FIG. 1A depicts the four plasmid expression vectors used for transfections. T7 RNA polymerase-dependent expression vectors (61) were prepared to direct expression of Edmonston wild-type N, P, L, or V genes in cells infected with MVA/T7 (62).

Although exemplified with measles virus, the invention is also applicable to other Morbilliviruses, including but not limited to canine distemper virus and rinderpest virus.

A consideration of the potential connection between measles virus attenuation and mechanisms involved in the control of gene expression and replication (30,60) led to the analysis of the V protein. V protein expression has been linked to viral pathogenicity (22,23,26–29) and also to control of gene expression and replication (21,26,27,35,45). The goal was to further analyze the effect of V protein on measles virus gene expression.

Before constructing mutant V protein expression vectors, the amino acid similarity between V proteins from several different Morbilliviruses was examined (FIG. 2). Regions of high amino acid identity may contain important functional domains, and that one or more of these conserved regions (CR) may participate in minireplicon repression. Alignment of V proteins from Edmonston wild-type measles virus, rinderpest virus, dolphin morbillivirus, and canine distemper virus revealed several conserved regions of notable sequence identity designated CR1–6 (shown in FIG. 2), in addition to confirming earlier observations (46) that the C-terminus contained seven cysteine residues spaced identically among the Morbilliviruses. Several of the CRs were targeted while generating mutant V protein vectors.

In addition to identifying regions containing high levels of identity, computer analysis was used to search for potential functional motifs and the literature was examined for additional clues concerning the possible location of potential measles virus V protein functional domains. The results of these analyses are illustrated on the alignment in FIG. 2. Several studies have located regions of V and P protein that influence the interaction with N protein. The extreme amino terminus (N-terminus) of V and P protein, located within CR1, contains sequences that mediate interaction with N protein (34) (FIG. 2) in a two-hybrid assay. Additional sequences involved in the V-N protein-protein interaction have been located between amino acids 204 to 230 (27,64) which encompasses CR4. The measles virus V protein zinc-binding domain (51) is in the C-terminus and probably requires at least several of the cysteine residues found in CR5 and CR6. At the N-terminal end of the cysteine-rich domain there is a well-conserved region containing basic amino acids (229–234) that is part of CR5. Near the same region (amino acid 225) in the measles virus V protein is an amino acid substitution found in Edmonston vaccine strains (wild-type glutamic acid to glycine (30)). Finally, in measles virus V protein there was a leucine repeat (amino acids 93–107) that was reminiscent of a leucine zipper motif (65,66). A number of these domains and motifs were attractive candidates for further study using the minireplicon system and V protein mutant expression vectors.

In addition to preparing a V protein expression vector (FIG. 1A), T7 expression plasmids were prepared for the three basic replication apparatus components including Edmonston wild-type N, P and L proteins. To eliminate any potential confusion due to C protein expression from the downstream translation initiation codon in the P and V protein vectors, the C protein open reading frame was modified to prevent translation of C protein. The C protein ATG codon was converted to ACG and the second codon in the C protein open reading frame was converted to a stop codon (TCA to TAA). These modifications were silent with respect to P and V proteins.

Indications that V protein may be involved in regulating measles virus mRNA transcription and genome replication (21,26,27,35,45) suggested an experiment to test whether a minireplicon system would respond to V protein expression. The minireplicon system was set up with Edmonston wild-type components so that V gene mutations that affect wild-type V protein function could be assessed, and potentially apply these findings to future genetic studies of virus attenuation using recombinant wild-type virus. The Edmonston wild-type measles virus-minireplicon (FIG. 1B, pMVwt107-CAT) was derived from the p107MV-CAT minireplicon (63) by converting the vaccine leader sequence in pMV107-CAT to the Edmonston wild-type leader sequence (60).

To determine if the wild-type components were capable of driving detectable minireplicon expression, HEp2 cells were transfected with minireplicon DNA and N, P and L protein expression vectors while simultaneously infecting with MVA/T7 (62) to provide T7 RNA polymerase. At 48 hours after transfection, cells were harvested and cell extracts were analyzed for CAT activity. The Edmonston wild-type minireplicon system readily produced CAT activity over background levels produced in negative controls that were transfected with all DNAs except the L polymerase protein expression vector (FIG. 1C, lanes 1 and 2, and data not shown). This indicated that the CAT activity produced during the transient expression assay was specific and was dependent upon an intact measles virus replication apparatus.

The minireplicon system was then used to determine whether expression of V protein had a detectable effect on minireplicon expression in a transient expression assay. Minireplicon assay transfections were performed with increasing amounts of V protein expression vector. The overall mass of DNA transfected was held constant by including the appropriate amount of expression vector lacking an insert. The effect of increasing the amount of V protein expression vector from 0 to 400 ng is shown in FIG. 1C. The positive control in lane 1 showed the amount of CAT activity obtained in the absence of V protein expression (FIG. 1C, lane 1). Lane 2 was a negative control that showed that CAT activity was undetectable when the L protein expression vector was omitted. Lanes 3–7 illustrate the negative effect of increasing amounts of V protein expression. Repression of CAT activity was evident at even the lowest amounts of V protein expression vector (lanes 3 and 4) and was very strong at higher amounts, virtually eliminating detectable minireplicon expression when 400 ng of V protein expression plasmid was transfected (lane 7). The two-fold increases in V protein expression vector used in lanes 3–7 also correlated well with observed decreases in relative CAT activity. These results clearly show that one aspect of V protein function can be observed with a minireplicon assay. This readily-detectable negative effect of V protein expression in a minireplicon assay provided a convenient format to further examine the minireplicon repression phenotype of V protein mutants.

Figure 3:
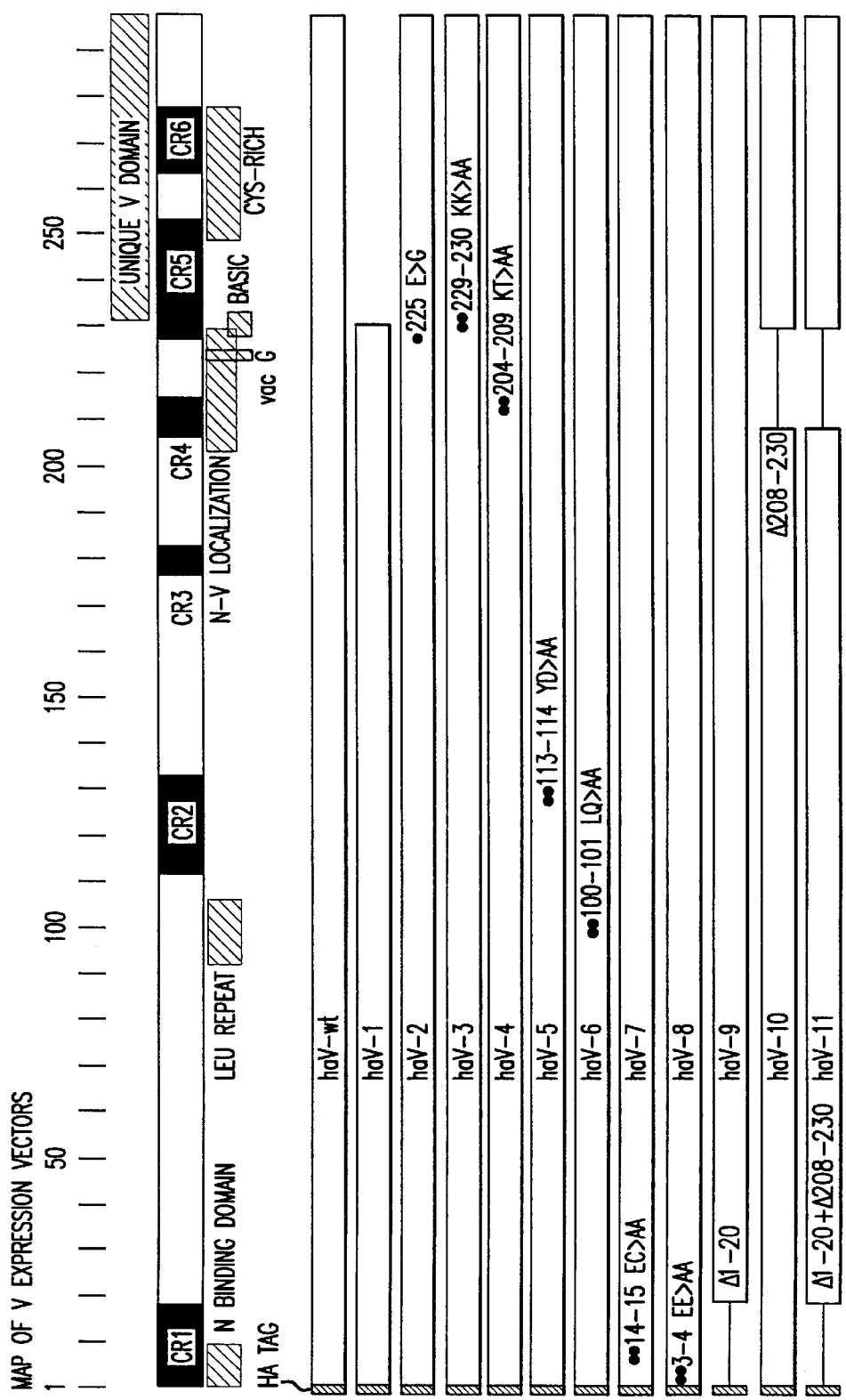
FIG. 3 depicts a map of mutant measles virus V protein expression vectors. The epitope-tagged V protein expression vectors used in these studies are shown diagramatically. Mutant V protein vectors were generated in a vector plasmid backbone that expressed V protein with an influenza virus HA tag (67) in place of the V protein initiator methionine. Sequence highlights are shown on a V protein map at the top of the Figure and are described more fully with respect to the description of FIG. 2 above. Wild-type (haV-wt) and mutant proteins (haV1-11) are illustrated below the V protein map. The HA tag is drawn as a crosshatched box at the amino-terminus and the remaining V protein sequence is drawn as an open box. Amino acid substitutions are indicated as black dots along with amino acid positions and amino acid changes. Deletion or truncation mutants are drawn with an interrupted V protein map.
Figure 4A:
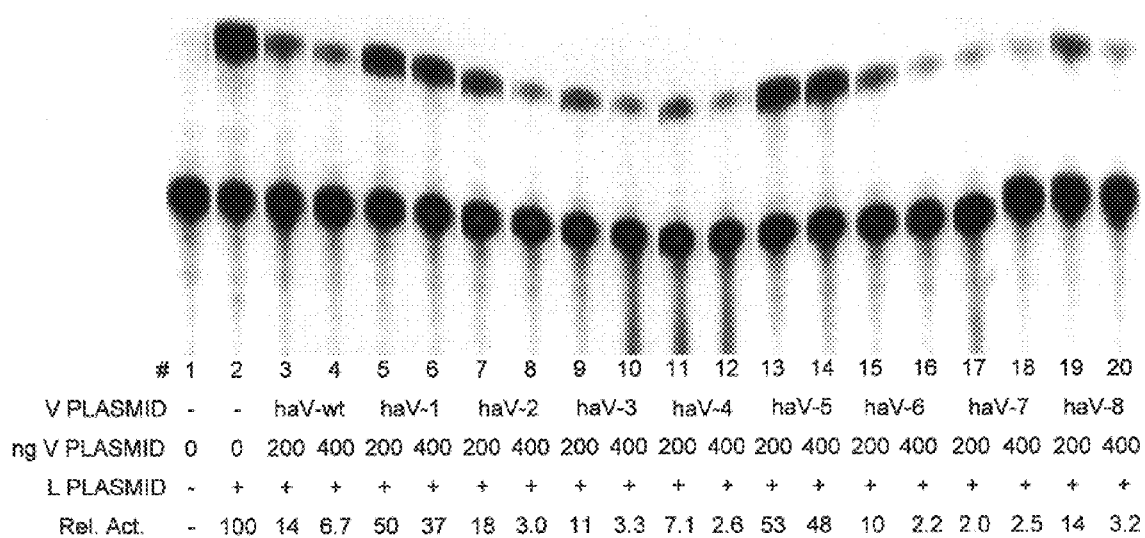
FIG. 4A depicts minireplicon repression by mutant measles virus V proteins, in the form of a CAT assay showing the results of a transient expression experiment testing the activity of V protein mutants (haV-1 to haV-8; see description for FIG. 3). The amount of V protein vector (200 or 400 ng) and the identity of the mutants are shown in FIG. 4A below the CAT assay. Relative activity is calculated as a percentage of the lane 2 that was derived from a transfection performed without any V protein expression vector. Lane 1 was a negative control performed without L protein.
Figure 4B:
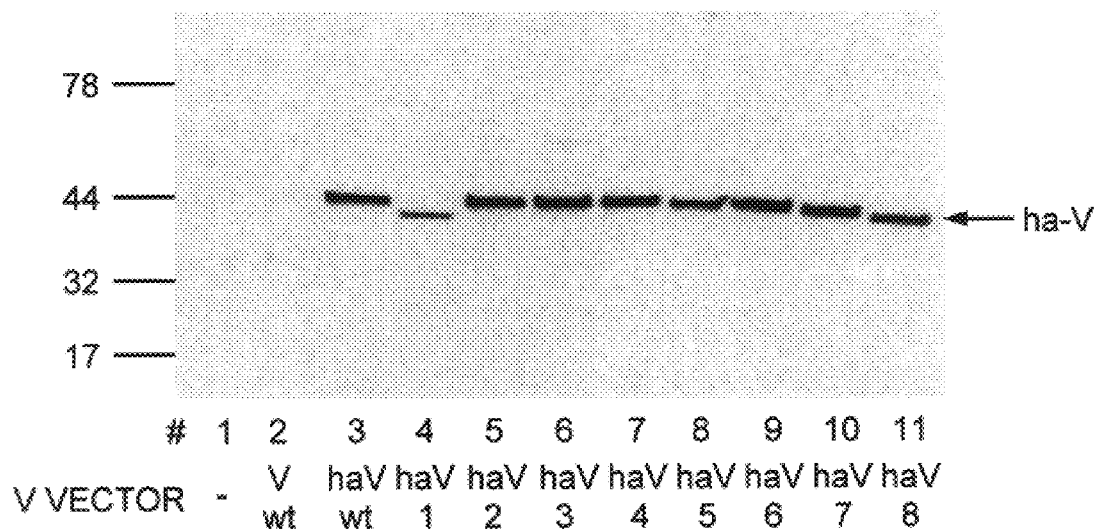
FIG. 4B depicts a Western blot performed to monitor V protein expression in transient expression experiments. Lanes 1 and 2 are negative controls derived from cells transfected in the absence of a V protein vector (lane 1) or transfected with a V protein vector that expresses a V protein without a tag. The Western blot was probed with anti-HA antibody.

To begin analyzing V protein mutants, the V protein expression vector (FIG. 1A) was modified to include an epitope tag at the amino-terminus of V protein (pMV-haV-wt; FIG. 3). This was done to facilitate Western blot detection of protein in lysates from transfected cells and to allow a relative comparison of the stability and steady-state levels of mutant V proteins. The initiator methionine codon of the wild-type V protein expression vector was replaced with the influenza hemagglutinin (HA) epitope tag (67). This modified V protein vector (pMV-haV-wt) also retained the base substitutions that prevent expression of C protein. Testing pMV-haV-wt in minireplicon experiments revealed that the presence of the N-terminal HA tag had no detectable effect on the ability of V protein to repress minireplicon activity (FIG. 4, lanes 1–4, and data not shown).

The first series of mutations introduced into pMV-haV-wt was directed at some of the sequence motifs illustrated in FIG. 2. One of these mutations resulted in a truncated V protein that lacked the unique V protein C-terminus containing the cysteine residues (amino acids 231–299 were deleted) (FIG. 3, pMV-haV-1). Plasmid pMV-haV-2 converted the wild-type V coding sequence to the Edmonston vaccine sequence (amino acid codon 225; glutamic acid to glycine). The remaining six mutations (pMV-haV numbers 3–8) were amino acid substitutions directed at some of the CRs. Initially, amino acid substitutions were introduced in an attempt to alter the function of specific domains in V protein without grossly altering the protein structure. Using a strategy suggested by the charge-to-alanine approach (68,69,70), mutations were introduced that primarily targeted two consecutive amino acid codons that specified charged or polar amino acid residues and converted them to codons encoding alanine.

Although this invention is exemplified by mutants having alanines rather than the wild-type residues, other nonconservative mutations of the wild-type residues are also within the scope of this invention. For example, aspartic acid is an acidic (negatively charged) molecule. Therefore, a nonconservative mutation will be one in which a substitution is made to an amino acid other than glutamic acid, which is also an acidic molecule. Suitable alternative amino acids include the amino acids lysine, histidine and arginine which are basic (positively charged) molecules. Suitable alternative amino acids further include the amino acids with nonpolar functional groups such as alanine, isoleucine, leucine, methionine, phenylalanine, proline, tryptophan and valine, and the amino acids with uncharged polar functional groups such as asparagine, cysteine, glutamine, glycine, serine, threonine and tyrosine.

Similarly, tyrosine is an uncharged polar molecule. Therefore, a nonconservative mutation will be one in which a substitution is made to an amino acid other than asparagine, cysteine, glutamine, glycine, serine and threonine, which are also uncharged polar molecules. Suitable alternative amino acids include the amino acids lysine, histidine and arginine which are basic (positively charged) molecules. Suitable alternative amino acids further include the amino acids with nonpolar functional groups such as alanine, isoleucine, leucine, methionine, phenylalanine, proline, tryptophan and valine, and the amino acids with acidic (negatively charged) functional groups such as aspartic acid and glutamic acid.

Analysis of the mutant V protein vectors 1 to 8 in a minireplicon assay is shown in FIG. 4A. The results indicate that two vectors (pMV-haV-1 and pMV-haV-5) had diminished ability to repress minireplicon activity. One mutant (hav-1) was a deletion mutant that lacked the unique C-terminus of V protein (amino acids 231–299); the second mutant (haV-5) contained substitution mutations at amino acids 113 and 114 (located in CR2; see FIG. 2). This suggested that this function could be partially mediated independently by CR2 and the C-terminus. Like the C-terminal truncation mutant, the CR2 mutant also retained residual repression activity.

Lanes 1 and 2 on FIG. 4A contained control samples. The transfection analyzed in Lane 1 lacked the L protein expression vector and revealed a low level of background CAT activity. The positive control in lane 2 showed the maximal activity observed in the absence of V protein. Repression mediated by 200 and 400 ng of wild-type V protein vector containing the HA tag (pMV-haV-wt) is shown in lanes 3 and 4. As described above, the N-terminal HA tag had little effect on the ability of V protein to repress the minireplicon, and in this experiment, 200 and 400 ng of hav-wt vector repressed minireplicon activity by about 7 and 16 fold, respectively. Most of the mutants repressed CAT activity nearly as effectively as the haV-wt vector, by reducing CAT activity to 20% or less (lanes 3, 7, 9, 11, 15, 17, 19) of the control activity (lane 2), when 200 ng of V protein vector was transfected. Two V protein vectors (pMV-haV-1, lanes 5 and 6; pMV-haV-5, lanes 13 and 14) were noticeably less effective at repressing minireplicon activity in this and repeat experiments. Plasmid pMV-haV-1 lacked the cystiene-rich V protein C-terminus, while pMV-haV-5 contained a double alanine substitution in CR2 (amino acids 113–114).

Both domains implicated in repression have interesting features. The C-terminus includes the zinc-binding domain and also contains an RNA binding domain (FIG. 5). The primary amino acid sequence of CR2 is noteworthy because computer models predict that a small cluster of charged residues may be positioned along one face of a proposed alpha helix (residues 114 D, 118 E, 121 K, 125 D). Thus, CR2 is potentially an amphipathic alpha helix similar to sequences that have been observed in some transcription factors (71).

The repression activity associated with CR2 also is interesting because this amino acid sequence is present in both the V and P proteins. The essential roles played by P protein-as polymerase subunit and nucleocapsid assembly factor (72) are quite distinct from the nonessential role of V protein in repression. Yet, these two proteins share a significant amount of amino acid sequence. CR2 may be a site of protein-protein interaction that functions differently in the context of V and P. Without being bound by theory, it may also be possible that the unique C-terminus of V protein imparts a tertiary structure to V protein that exposes CR2, in turn allowing it to function as a repressor domain, while in P protein this domain is sequestered.

To determine if the reduction in repression caused by mutant haV-1 or haV-5 simply correlated with poor protein expressions a Western blot was performed using anti-HA antibody to estimate the relative abundance of V protein in transfected cells (FIG. 4B). Cells for this experiment were transfected exactly as performed during minireplicon experiments, so that the cells contained N, P and L proteins as well as V protein. Tagged V proteins were detectable in all transfected-cell extracts except for two negative controls. No V protein vector was transfected in cells used to make extract analyzed in lane 1, and in lane 2, the cells were transfected with the vector encoding the V protein that does not include an epitope tag. The protein detected in lane 3 was the HA-tagged wild-type V protein. The protein in lane 4 was the truncation mutant that lacked the C-terminus and its mobility was noticably altered. The remaining proteins were mutants (as described above) that contained amino acid substitutions (FIG. 4B, lanes 5–11). Several of these proteins had small but noticeable mobility changes in this 12% polyacylamide gel (for example, lanes 10 and 11). However, this was not unexpected, since charged and polar residues were replaced by alanines in these proteins. The relative abundance of all the proteins was judged to be quite similar, except that hav-1 (lane 4) was lower in this experiment and this was reproducible in repeat experiments. This suggested that the reduced repression activity of haV-1 may result from lower proteins levels, while the reduced repression activity of haV-5 was not caused by an unstable protein.

Figure 4C:
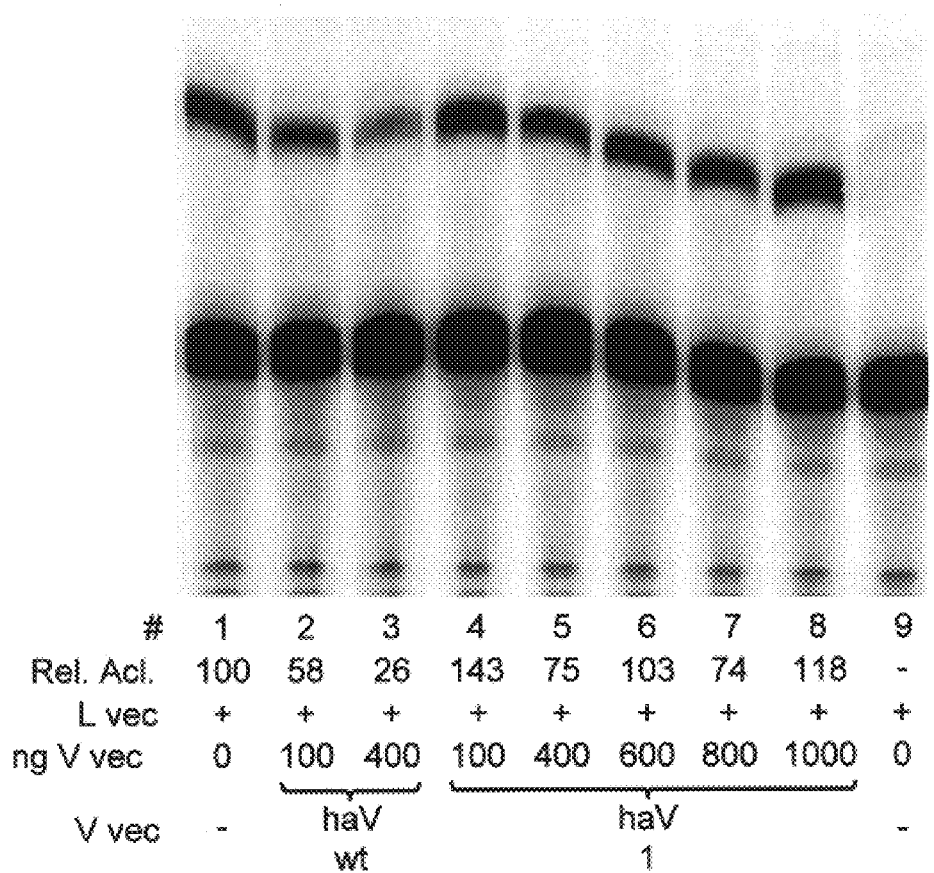
FIG. 4C depicts an analysis of minireplicon repression by haV-1 using increasing amounts (100 ng to 1 μg) of the expression vector.

To further examine the possibility that hav-1 repressed poorly simply because it was unstable, a minireplicon assay was performed with increasing amounts of V protein vector to help supplement the intracellular quantity of haV-1 protein (FIG. 4C). This minireplicon experiment was performed as described above, except that the maximum amount of V protein vector was increased from 400 ng to 1 μg. The mass of DNA was held constant in all transfections by including the appropriate quantity of vector backbone DNA (lacking insert). FIG. 4C, lane 1, was the positive control that was performed without added V protein vector. Lanes 2 and 3 show the effect of adding wild-type ha-V vector at 100 (lane 2) and 400 (lane 3) ng, which reduced activity in this experiment to 58% and 26%, respectively. Addition of increasing amounts of haV-1 had little effect on the activity-of MV-CAT and no obvious trend was observed for correlating increasing mass of haV-1 vector with greater levels of repression. This suggested that the diminished repression activity of haV-1 was not simply due to reduced intracellular protein levels and was instead an effect of the loss of the C-terminus.

A region containing a high content of basic amino acids in the N-terminal third of the SV5 V protein mediates RNA binding (73). A homologous region is not apparent in measles virus V protein (73), but the possibility was examined that measles virus V protein may also bind RNA through the zinc finger-like sequences in the C-terminus (FIG. 5).

To assess the RNA binding activity of V protein, a polyribonucleotide homopolymer binding assay was used (FIG. 5A) that has been used successfully to study several cellular RNA binding proteins (74–77). A number of RNA binding proteins display characteristic affinity for polyribonucleotide homopolymers. For example, the cellular hnRNP U protein binds with relatively high affinity to poly(G) and poly(U,) but binds little if at all to poly(A) or poly(C) (75). This-concept was used to determine if V protein in transfected cell extracts could be captured on homopolymer resins. Cells were transfected with all of the expression vectors (N, P, L, V and minireplicon) used in the minireplicon transfection and were then infected with MVA/T7. Cytoplasmic cell lysates were prepared 48 hours later and incubated for 30–60 minutes at 4° C. with agarose beads linked to one of the four polyribonucleotide homopolymers. The beads were collected by centrifugation, then resuspended and washed three times in cell lysis buffer. The bound proteins were eluted from the beads by boiling in SDS-gel loading buffer.

Initially, to test the assay, the ability to capture a known RNA binding protein expressed from a transfected plasmid was examined. Accordingly, proteins eluted from the four different resins were analyzed by Western Blot using monoclonal antibody specific for N protein (FIG. 5B). N protein was detected readily in samples bound to poly(G) and poly(U) (lanes 2 and 4). The amount of N protein bound to poly(G) was generally greater in this assay and several repeat experiments. Little or no N protein was captured with poly(A) or poly(C).

The experiment was repeated as described above to analyze the ability of haV protein to interact with the homopolymer resins (FIG. 5B, lanes 5–8). Analysis of a Western blot with anti-HA antibody revealed results that were similar to the results obtained after analysis of N protein (FIG. 5B, lanes 1–4). The poly(G) and poly(U) resins both displayed affinity for haV (lanes 6 and 8). V protein bound best to poly(G) and more weakly to poly(U), while binding poorly to poly(A) or poly(C). In some experiments, a very weak band was seen, indicating a low affininty interaction with poly(A); however, usually this interaction is undetectable.

The fact that V protein bound readily to poly(G) and poly(U) and not well to poly(A) and poly(C) indicated that the assay was not simply measuring affinity for polyanion resins, and also showed that V protein demonstrated a preference for two polynucleotides. Both V protein and N protein preferred poly(G) and poly(U) (FIG. 5); this is a feature displayed by a number of cellular RNA binding proteins (74,76,77).

The fact that the binding profile of haV protein was quite similar to N protein raised the possibility that V protein was captured indirectly on poly(G) and and poly(U) resins through interaction with N protein, rather then a direct interaction with RNA. To examine this possibility, cells were transfected only with the haV protein expression vector and cell extracts were prepared and treated as described above. Analysis by Western blot showed that haV protein (FIG. 5B, lanes 9–12) was again bound to poly(G) and poly(U). This indicated that the interaction of V protein with homopolymer resins required no other viral protein. In fact, in the absence of other viral proteins, greater quantities of V protein were usually bound to poly(G) and poly(U) (compare lanes 6 to 10 and 8 to 12). This suggested that one of the other viral proteins may slightly interfere with the interaction between V protein and the polyribonucleotides.

A limited analysis of conditions that influence the binding of haV to poly(G) was also performed (FIG. 5B, lanes 13–16). Addition of 10 mM EGTA or EDTA (lanes 14 and 15) to the binding reaction reduced the quantity of V-protein bound to poly(G). Addition of yeast RNA competitor (lane 16) to the binding reaction (25 μg per ml) had little effect on binding. However, this was not especially surprising, because the cytoplasmic extracts already contained significant quantities of cellular RNA and addition of yeast RNA likely had little impact. These results suggest that binding of V protein to poly(G) is stimulated by divalent cations and is a relatively specific interaction, because addition of a non-specific RNA (yeast RNA) did not seem to diminish the amount of V protein bound to the resin.

To determine if RNA binding could be correlated with the ability to repress minireplicon activity, the poly(G) binding assay was next used to analyze the RNA binding activity of the haV protein mutants. The haV protein mutants (FIG. 3) were expressed in cells without any other viral proteins. Crude cytoplasmic extracts were prepared and bound to poly(G) resins as described above, and bound proteins were analyzed by Western blotting (FIG. 6). As shown earlier, haV was captured by poly(G) and detected by anti-HA antibody on a Western blot (lane 2), while a sample containing V protein without an HA-tag (lane 1) generated no background signal. Analysis of the mutant proteins revealed similar levels of poly(G) binding activity for most of the V proteins (lanes 4–13). The exception was mutant haV-1. Very low levels of this mutant protein bound to poly(G). This clearly indicated that the protein was defective for binding (lane 3). The low but detectable levels of binding by haV-1 indicated that RNA binding activity was substantially reduced, but not entirely eliminated. These results demonstrated that most of the mutants retained RNA binding activity nearly equivalent to wild-type haV. One of the two mutants that was defective for minireplicon repression (haV-5) bound poly(G) as well as wild-type hav, while the other mutant (haV-l) exhibited significantly reduced poly(G) binding activity. This suggested that there may be a correlation between minireplicon repression and RNA binding activity mediated by the unique C-terminus of V protein. In turn, this suggested that V protein RNA binding activity may play a regulatory role in measles virus gene expression and replication.

A potential connection between RNA binding activity associated with V protein and minireplicon repression could be drawn from the results that showed that a V protein mutant lacking the C-terminus cysteine-rich region bound RNA poorly and was also a less effective minireplicon repressor.

In a separate experiment, minireplicon repression was shown not to correlate with the ability of V protein to bind N protein. Formation of a V-N protein complex was not necessary for V protein-mediated minireplicon repression; V protein mutants haV-9 and haV-11 (FIG. 3) failed to interact with N protein, but retained full repression activity (data not shown).

Analysis of V protein mutants suggested that the C-terminus was required for high affinity RNA binding. Deletion of this region that includes the zinc-binding domain (51) greatly reduced the amount of protein that could be collected on poly(G) resins, but did not entirely eliminate all binding. This may suggest that there is a second weak RNA binding domain in V protein. Without being bound by the following, an attractive possibility is that the zinc finger-like domain in the C-terminus forms one important component of a nucleic acid binding domain, and a second domain in V protein cooperates with the C-terminus to create a higher affinity binding site.

These studies of RNA binding also showed that V protein could interact with RNA without any additional viral proteins present in crude cell extracts. This suggests that V protein directly bound to RNA. This conclusion is not absolute, because it remains possible that V protein interacts with a cellular protein that in turn is responsible for binding to RNA. If this model were true, the data indicates that the C-terminus may mediate the protein-protein interaction responsible for interaction with a cellular factor. Purified recombinant V protein will be important to further examine whether V protein directly binds RNA.

Figure 6:
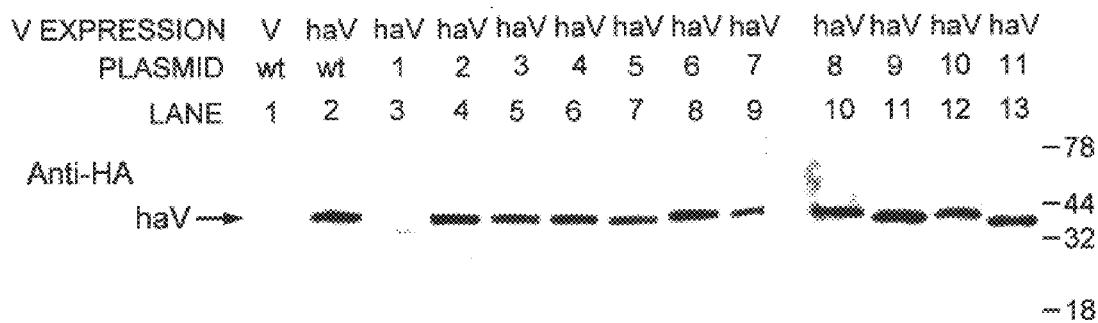
FIG. 6 depicts RNA binding by mutant measles virus V proteins. The polyribonucleotide homopolymer binding assay described in FIG. 5 was used for analysis of mutant measles virus V proteins (haV 1–11, lanes 3–13; see description for FIG. 3). In this experiment, the cells were transfected with only V expression vectors. The cell extract examined in lane 1 was a negative control that contained V protein that did not contain an epitope tag. Poly(G) was used to test all of the mutant proteins.

Although the mutant haV-5 protein was defective for minireplicon repression (FIG. 4), it bound to RNA (FIG. 6) as well as the wild-type protein. Thus, the minireplicon repression activity associated with CR2 did not readily correlate with the other two activities analyzed (RNA binding and interaction with N protein). For CR2 to function effectively as a repressing motif, it may require an intact RNA binding domain in the C-terminus of V protein. V protein may be similar to some RNA polymerase II transcription factors and it has a modular structure (78).

Figure 7:
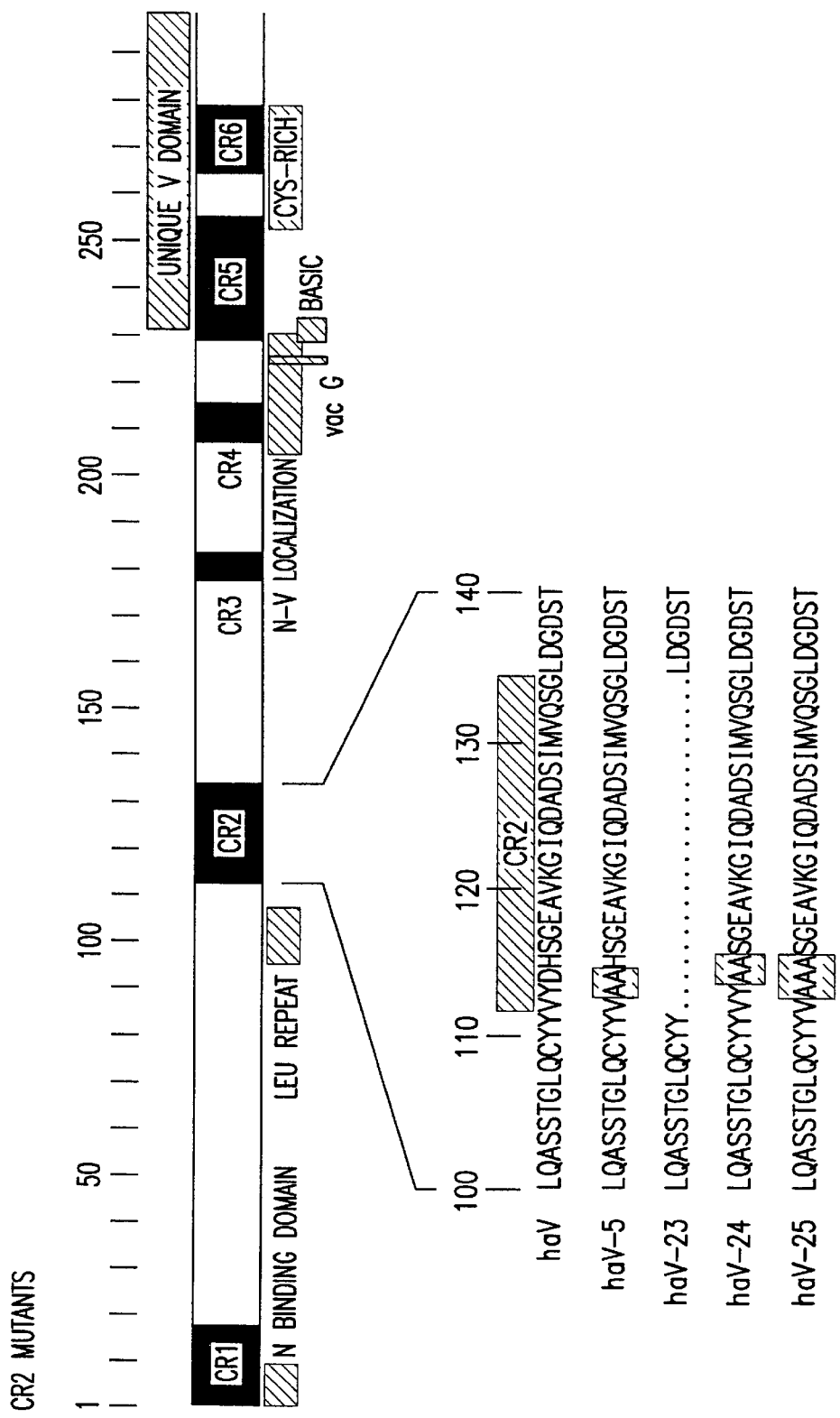
FIG. 7 depicts a comparison of the amino acid sequences in CR2 (amino acids 100–140) for wild-type measles virus V protein, designated haV (SEQ ID NO:7); a mutant where the tyrosine at amino acid 113 and the aspartic acid at amino acid 114 are substituted with alanines, designated haV-5 (SEQ ID NO:8); a mutant where amino acids 112–134 are deleted, designated haV-23 (SEQ ID NO:9); a mutant where the aspartic acid at amino acid 114 and the histidine at amino acid 115 are substituted with alanines, designated haV-24 (SEQ ID NO:10); and a mutant where the tyrosine at amino acid 113, the aspartic acid at amino acid 114 and the histidine at amino acid 115 are substituted with alanines, designated haV-25 (SEQ ID NO:11).
Figure 8:
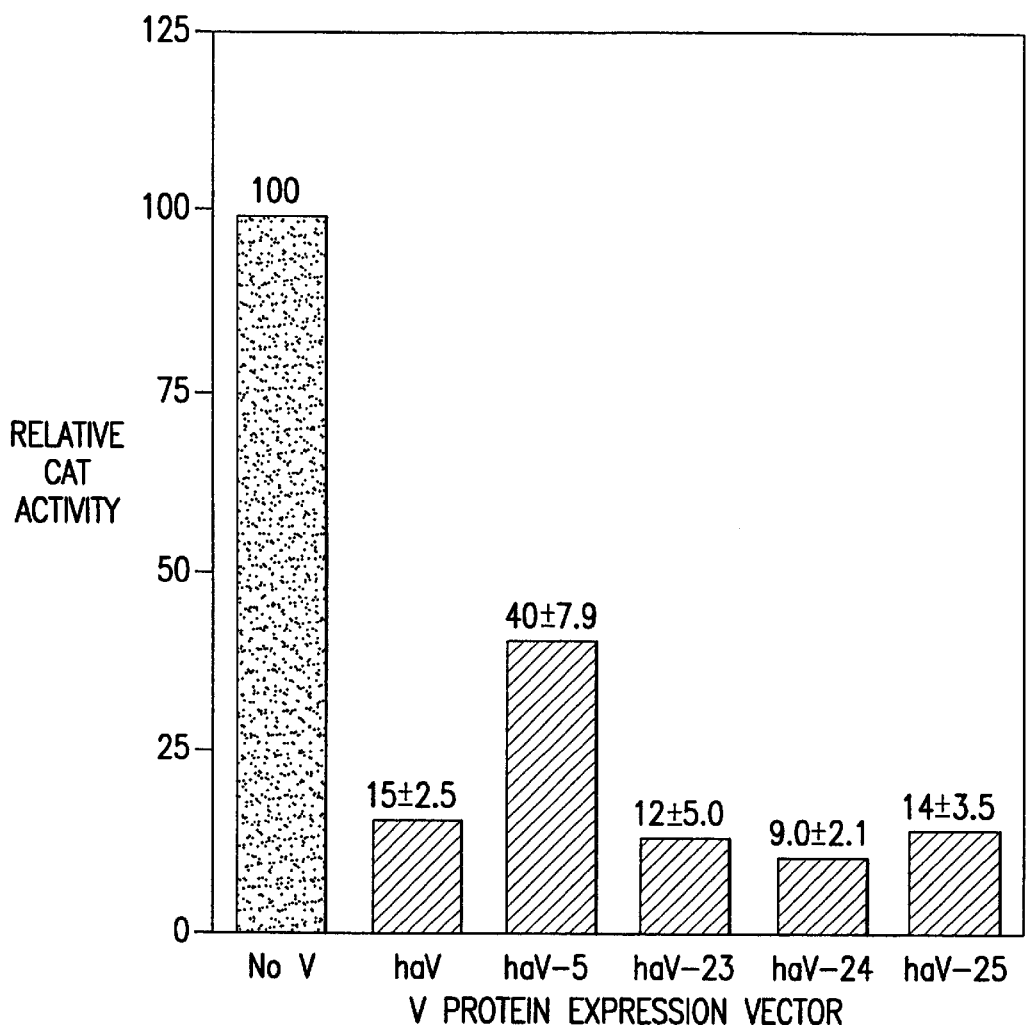
FIG. 8 depicts the effect of the CR2 mutations described in FIG. 7 in a CAT assay that demonstrated the effect of V protein expression on minireplicon activity in a transient expression assay. Bar 1 was the positive control obtained from cells that were transfected with all plasmid vectors (N, P and L) necessary to drive minireplicon expression. Bar 2 was identical to bar 1, except that the cells were also transfected with an expression vector encoding haV; in bars 3–6, the cells were transfected with expression vectors encoding the indicated CR2 mutations. Relative CAT activity was calculated based on 100% activity in bar 1.

To more fully test the possibility that CR2 was directly involved in repression, this domain (amino acids 112–134) was deleted to generate haV-23 (FIG. 7; SEQ ID NO:9). Surprisingly, this deletion did not greatly affect repression activity (FIG. 8). The fact that CR2 could be deleted without affecting repression argues that CR2 does not contain a domain that actively participates in repression. Instead, it appears that the defect caused by the substitution of amino acids 113 plus 114 found in haV-5 (FIGS. 7 and 8) generated a dominant-negative effect (previous Western blot analysis indicated that the defect in repression was not caused by haV-5 instability).

Without being bound by theory, the YD to AA substitution in haV-5 generated a subtle alteration in the tertiary structure of V protein that partially blocks repression activity. Alternatively, there may be interaction between V protein and other viral proteins or cellular proteins. The double alanine substitution may favor a protein-protein interaction that inhibits repression activity or sequesters V protein in an inactive protein complex.

The concept that the weak repression phenotype was caused by a dominant-negative effect created by the double alanine substitution was tested further by making additional amino acid substitutions that were very similar but distinct from the mutations found in haV-5 (FIG. 7). The original YD to AA substitution in haV-5 was engineered in a well-conserved motif consisting of V<u>YDH</u> located at the amino boundary of CR2 (FIG. 2). This motif was identical in V protein sequences from measles virus, canine distemper virus, rinderpest virus and dolphin morbillivirus. In mutant haV-24 (SEQ ID NO:10), the VYDH sequence was converted to VYAA, and in mutant haV-25 (SEQ ID NO:11), VYDH was converted to VAAA. Both of these mutants repressed MV minireplicon gene expression as well as the wild-type haV protein (FIG. 8). This implies that the haV-5 defect is very specific for the VYDH to VAAH substitution.

Figure 9:
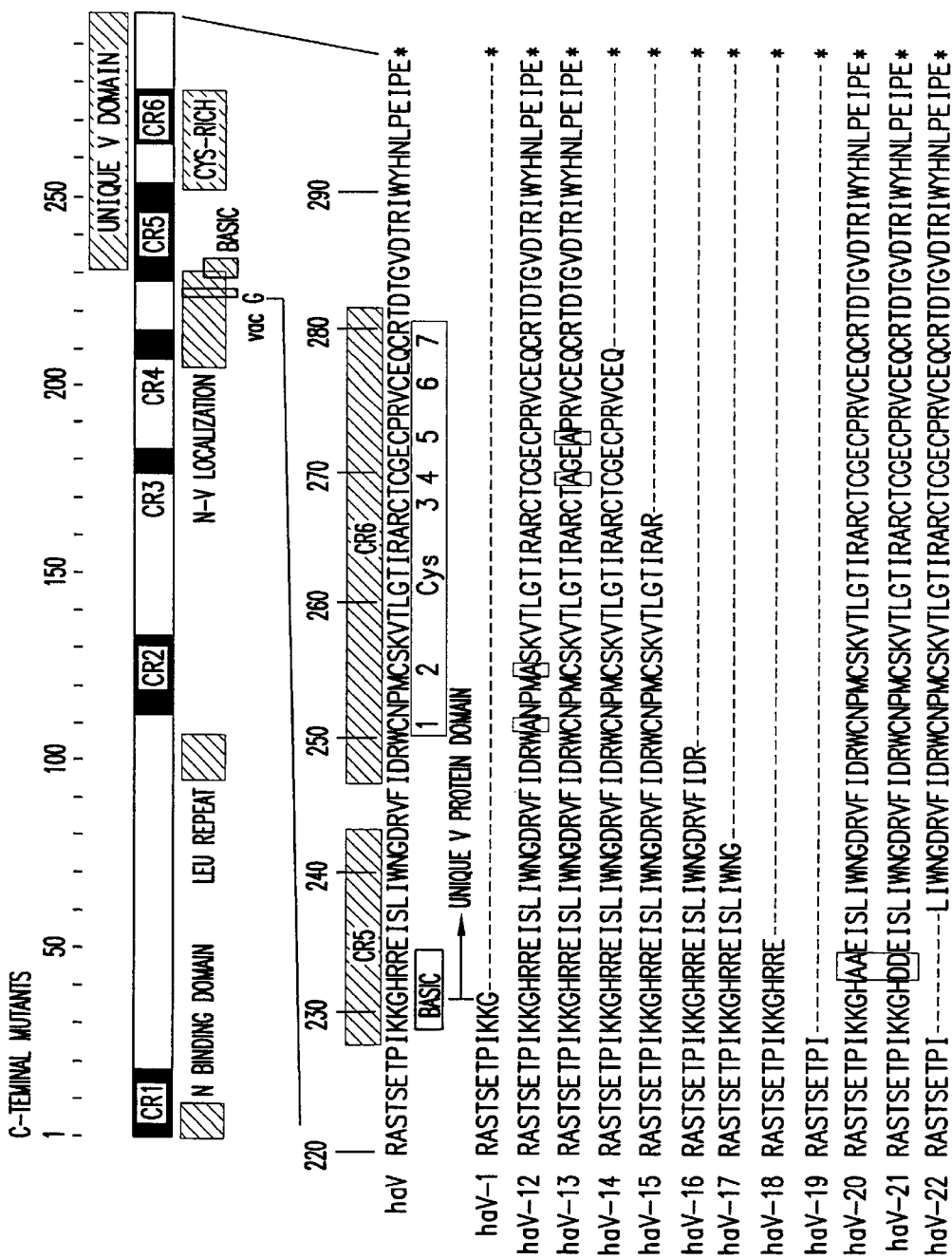
FIG. 9 depicts a comparison of the amino acid sequences in the C-terminus (amino acids 220–299) for wild-type measles virus V protein, designated haV (SEQ ID NO:12); a mutant where amino acids 232–299 are deleted, designated haV-1 (SEQ ID NO:13); a mutant where the cysteines at amino acids 251 and 255 are substituted with alanines, designated haV-12 (SEQ ID NO:14); a mutant where the cysteines at amino acids 269 and 272 are substituted with alanines, designated haV-13 (SEQ ID NO:15); a mutant where amino acids 279–299 are deleted, designated haV-14 (SEQ ID NO:16); a mutant where amino acids 267–299 are deleted, designated haV-15 (SEQ ID NO:17); a mutant where amino acids 250–299 are deleted, designated haV-16 (SEQ ID NO:18); a mutant where amino acids 243–299 are deleted, designated haV-17 (SEQ ID NO:19); a mutant where amino acids 236–299 are deleted, designated haV-18 (SEQ ID NO:20); a mutant where amino acids 229–299 are deleted, designated haV-19 (SEQ ID NO:21); a mutant where the arginines at amino acids 233 and 234 are substituted with alanines, designated haV-20 (SEQ ID NO:22); a mutant where the arginines at amino acids 233 and 234 are each substituted with aspartic acid, designated haV-21 (SEQ ID NO:23); and a mutant where amino acids 229–237 are deleted, designated haV-22 (SEQ ID NO:24).

The possibility that a C-terminal zinc-finger-like domain plays a role in repression was examined further by introducing amino acid substitutions in pairs of cysteine residues in the C-terminus (FIG. 9). Mutant haV-12 (SEQ ID NO:14) was generated with cysteine residues 1 and 2 (amino acids 251 and 255) converted to alanines. Similarly, mutant haV-13 (SEQ ID NO:15) was generated with C-terminal cysteine residues 4 and 5 (amino acids 269 and 272) replaced with alanines. Cysteine residues were mutated in pairs expecting that this would significantly alter a zinc-finger-like structure in the C-terminus and produce a readily detectable alteration in repression activity.

Surprisingly, CAT expression studies of these mutants (FIG. 10) revealed that they were only mildly affected by the cysteine substitutions; both haV-12 and haV-13 retained a significant. proportion of wild-type haV protein repression activity (about 65% of wild-type). This result was somewhat unexpected; it was predicted that substitution of zinc-coordinating cysteine residues would abolish repression. Possibly, substitution of only two out of seven cysteine residues did not completely disrupt the putative zinc-finger nucleic acid binding structure. Alternatively, it is possible that the putative zinc-finger motif plays a less prominent role in repression than previously predicted. Thus, two additional series of mutations were prepared to further examine the role of the C-terminus in repression.

In one set of mutations, small incremental deletions were made starting from the C-terminus (haV-14 through haV-19; SEQ ID NOS:16–21). The smallest deletion (haV-14) removed 21 amino acids from the C-terminus, whereas the largest deletion (haV-19) removed 71 amino acid residues. Mutant haV-19 was constructed even though it is nearly identical to hav-1 (FIG. 9; SEQ ID NO:13), because the deletion in haV-19 removed several additional amino acids that were part of the small basic motif located between amino acids 229–234, and the phenotype of haV-19 could be viewed as verification of the mutant phenotype displayed by haV-1.

Figure 10:
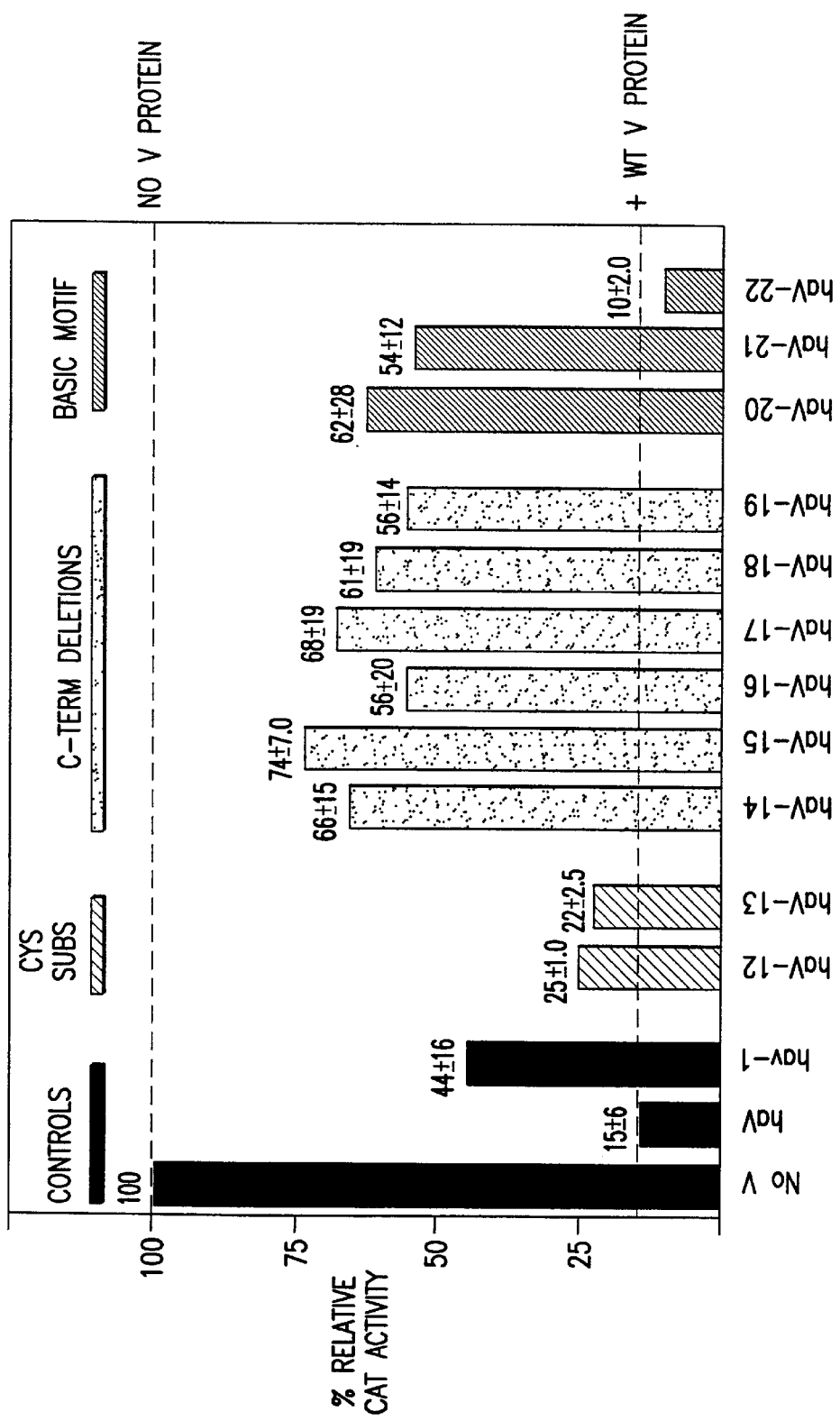
FIG. 10 depicts the effect of the C-terminal mutations described in FIG. 9 in a CAT assay that demonstrated the effect of V protein expression on minireplicon activity in a transient expression assay. Bar 1 was the positive control obtained from cells that were transfected with all plasmid vectors (N, P and L) necessary to drive minireplicon expression. Bar 2 was identical to bar 1, except that the cells were also transfected with an expression vector encoding haV; in bars 3–14, the cells were transfected with expression vectors encoding the indicated C-terminal mutations. Relative CAT activity was calculated based on 100% activity in bar 1.

Analysis of the C-terminal mutants in the minireplicon assay revealed that the large deletion mutants (haV-1 and haV-19) behaved similarly; they repressed minireplicon gene expression only about two fold or less instead of the 5–8 fold repression induced by wild-type haV (FIG. 10). Interestingly, the diminished repression activity displayed by the large deletions was reproduced by all of the smaller truncation mutants. Even the smallest C-terminal deletion (haV-14) resulted in a V protein that repressed only about two fold. This result implied that the integrity of the extreme C-terminus is essential for full repression activity.

In addition to analyzing the effect of the C-terminal deletion mutations, several additional mutations were generated to examine the possibility that the basic motif (KKGHRR; amino acids 229–237, SEQ ID NO:12) at the beginning of the unique V protein C-terminus played some role in repression. Conversion of the two arginine residues to alanine (haV-20; SEQ ID NO:22) or aspartic acid (haV-21; SEQ ID NO:23) had an effect that was similar to the C-terminal deletion mutations. The two substitution mutants repressed minireplicon expression by an average of only 1.5 to 3 fold whereas wild-type V protein repression normally ranged from 5–8 fold (FIG. 10). These results implied that perturbation of the basic motif also disrupted normal V protein repression function.

This result was examined further by deleting the basic motif (FIG. 9, haV-22; SEQ ID NO:24), while leaving the remainder of the C-terminus intact. Surprisingly, one preliminary experiment has indicated that deletion of the basic motif had no discernable effect on repression activity; haV-22 repressed CAT activity by about nine-fold (FIG. 10). Taken together, these results suggest that amino acid substitutions in the basic motif produce a dominant-negative effect on repression activity possibly by causing an unfavorable change in protein tertiary structure. On the other hand, deletion of the basic motif produced little change in the ability of V protein to repress minireplicon gene expression.

The mechanism of measles virus V protein minireplicon repression is unknown. The results suggest that the mechanism does not require interaction with N protein, but does involve interaction with RNA. RNA binding could result in reduced CAT levels in a minireplicon assay through a number of different mechanisms. For example, RNA binding activity could repress translation if V protein binds viral mRNAs. V protein could also influence rates of encapsidation if it binds nascent viral RNAs and prevents association of RNA with N protein. Conversely, it could somehow stimulate nucleocapsid assembly, thereby forcing the minireplicon system to overproduce genomic-length RNA at the expense of mRNA. V protein could also be envisioned as analogous to a transcription factor that binds at or near the promoter and represses transcription. If V protein is analogous to a transcription factor, it could be a regulator of the switch that balances genome synthesis and mRNA synthesis.

Dissection of V protein functions provides a basis for introducing attenuating mutations in candidate Morbillivirus strains for use in immunogenic compositions. Published studies have shown that elimination of V protein expression results in attenuated viral replication (19,22,23,26–29). Varying degrees of attenuation are introduced by targeting amino acid substitutions to specific domains of V protein, rather then eliminating expression. For example, partial loss of V protein repression function is achieved by mutation of one or more cysteine residues in the unique C-terminus. Substitutions in a region shared by P and V are suitable, such as the alanine substitutions in CR2, if they have an effect on V protein function without much effect on P protein. These mutations are evaluated using the reverse genetic systems for "rescue", as described in the art (19,79,80,81).

The reverse genetics system must be used to generate an infectious Morbillivirus containing the mutations of this invention, because naked genomic RNA cannot serve as a template for transcription and replication. Instead, these genomic sequences are recognized only when they are entirely encapsidated by the N protein into the nucleocapsid structure. It is only in that context that the genomic and antigenomic terminal promoter sequences are recognized to initiate the transcription or replication pathways.

Transcription and replication of negative-sense, single-stranded RNA viral genomes are achieved through the enzymatic activity of a multimeric protein acting on the ribonucleoprotein core (nucleocapsid). All Morbilliviruses require the three viral proteins, N, P and L, for these pathways to proceed.

The mutations described herein are introduced into Morbillivirus strains by using site-directed mutagenesis. One or more mutations as defined herein are introduced into a Morbillivirus strain. Cumulative effects of different combinations of mutations can be assessed.

This invention is exemplified with the minireplicon system. The changes in nucleotide sequences encoding the mutations to the CR2 and the C-terminus of the V protein of Morbilliviruses (as well as to the promoter region and L protein, the N, P and/or C proteins and/or the F gene-end signal of measles virus) can be inserted readily into full length viruses using techniques known in the art. The mutations are introduced by standard recombinant DNA methods into a DNA copy of the viral genome. This may be a wild-type or a modified viral genome background, thereby generating a new virus. Infectious clones or particles containing these mutations are generated using the cDNA rescue system, which has been applied to a variety of negative-sense RNA viruses, including Sendai virus (82); measles virus (83,88); respiratory syncytial virus (84); PIV-3 (85); rabies (86); vesicular stomatitis virus (VSV) (87); and rinderpest virus (89); these references are hereby incorporated by reference.

Briefly, all Morbillivirus rescue systems can be summarized as follows: Each requires a cloned DNA equivalent of the entire viral genome placed between a suitable DNA-dependent RNA polymerase promoter (e.g., the T7 RNA polymerase promoter) and a self-cleaving ribozyme sequence (e.g., the hepatitis delta ribozyme) which is inserted into a propagatable bacterial plasmid. This transcription vector provides the readily manipulable DNA template from which the RNA polymerase (e.g., T7 RNA polymerase) can faithfully transcribe a single-stranded RNA copy of the viral antigenome (or genome) with the precise, or nearly precise, 5' and 3' termini. The orientation of the viral genomic DNA copy and the flanking promoter and ribozyme sequences determine whether antigenome or genome RNA equivalents are transcribed. Also required for rescue of new virus progeny are the virus-specific transacting proteins needed to encapsidate the naked, single-stranded viral antigenome or genome RNA transcripts into functional nucleocapsid templates: the viral nucleocapsid (N) protein, the polymerase-associated phosphoprotein (P) and the polymerase (L) protein. These proteins comprise the active viral RNA-dependent RNA polymerase which must engage this nucleocapsid template to achieve transcription and replication.

Typically, these viral trans-acting proteins are generated from one or more plasmid expression vectors encoding the required proteins, although some or all of the required trans-acting proteins may be produced within mammalian cells engineered to contain and express these virus-specific genes and gene products as stable transformants.

The typical (although not necessarily exclusive) circumstances for rescue include an appropriate mammalian cell milieu in which T7 polymerase is present to drive transcription of the antigenomic (or genomic) single-stranded RNA from the viral genomic cDNA-containing transcription vector. Either cotranscriptionally or shortly thereafter, this viral antigenome (or genome) RNA transcript is encapsidated into functional templates by the nucleocapsid protein and engaged by the required polymerase components produced concurrently from co-transfected expression plasmids encoding the required virus-specific trans-acting proteins. These events and processes lead to the prerequisite transcription of viral mRNAs, the replication and amplification of new genomes and, thereby, the production of novel viral progeny, i.e., rescue.

For the rescue of the non-Morbilliviruses rabies, VSV and Sendai, T7 polymerase is provided by recombinant vaccinia virus VTF7–3. This system, however, requires that the rescued virus be separated from the vaccinia virus by physical or biochemical means or by repeated passaging in cells or tissues that are not a good host for poxvirus. For measles virus cDNA rescue (and presumably for other Morbilliviruses), this requirement is avoided by creating a cell line that expresses T7 polymerase, as well as viral N and P proteins. Rescue is achieved by transfecting the genome expression vector and the L gene expression vector into the helper cell line. Advantages of the host-range mutant of the vaccinia virus, MVA-T7, which expresses the T7 RNA polymerase, but produces little or no infectious progeny in mammalian cells, are exploited to rescue measles virus and other Morbilliviruses. After simultaneous expression of the necessary encapsidating proteins, synthetic full length antigenomic viral RNA are encapsidated, replicated and transcribed by viral polymerase proteins and replicated genomes are packaged into infectious virions. In addition to such antigenomes, genome analogs have now been successfully rescued for Sendai and PIV-3 (85,90).

The rescue system thus provides a composition which comprises a transcription vector comprising an isolated nucleic acid molecule encoding a genome or antigenome of a Morbillivirus. The nucleic acid molecule contains at least one mutation in the region corresponding to amino acids 112–134 of the measles virus V protein (and, optionally, other mutations described herein), together with at least one expression vector which comprises at least one isolated nucleic acid molecule encoding the trans-acting proteins necessary for encapsidation, transcription and replication (e.g., N, P and L for a Morbillivirus). Host cells are then transformed, infected or transfected with the at least two expression vectors just described. The host cells are cultured under conditions which permit the co-expression of these vectors so as to produce the infectious modified virus.

The rescued infectious virus is then tested for its desired phenotype (reduced repression by V protein, temperature sensitivity, cold adaptation, plaque morphology, and transcription and replication attenuation), first by in vitro means. The mutations in the N, P or C genes or the F gene-end signal of measles virus are also tested using the minireplicon system where the required trans-acting encapsidation and polymerase activities are provided by wild-type or vaccine helper viruses, or by plasmids expressing the N, P and different L genes harboring gene-specific attenuating mutations (63,83).

If the attenuated phenotype of the rescued virus is present, challenge experiments are conducted with an appropriate animal model. Non-human primates provide the preferred animal model for the pathogenesis of human disease. These primates are first immunized with the attenuated, recombinantly-generated virus, then challenged with the wild-type form of the virus. Monkeys are infected by various routes, including but not limited to intranasal, intratracheal or subcutaneous routes of inoculation (91). Experimentally infected rhesus and cynomolgus macaques have also served as animal models for studies of vaccine-induced protection against measles (92).

Protection is measured by such criteria as disease signs and symptoms, survival, virus shedding and antibody titers. If the desired criteria are met, the recombinantly-generated virus is considered a viable candidate vaccine or immunogenic composition for testing in humans. The "rescued" virus is considered to be "recombinantly-generated", as are the progeny and later generations of the virus, which also incorporate the mutations.

Even if a "rescued" virus is underattenuated or overattenuated relative to optimum levels for vaccine use, this is information which is valuable for developing such optimum strains.

Optimally, a codon containing a point mutation may be stabilized by introducing a second or a second plus a third mutation in the codon without changing the amino acid encoded by the codon bearing only the point mutation. Infectious virus clones containing the stabilizing mutations are also generated using the cDNA "rescue" system described above.

Previously, in published International patent application WO98/13501 (93), which is hereby incorporated by reference, the generation and isolation of recombinantly-generated, attenuated, nonsegmented, negative-sense, single-stranded RNA viruses of the Order Mononegavirales (such as measles virus) having at least one attenuating mutation in the 3' genomic promoter region and having at least one attenuating mutation in the RNA polymerase gene was disclosed.

Specifically, these mutations comprised:
(1) at least one attenuating mutation in the 3' genomic promoter region selected from the group consisting of nucleotide 26 (A→T), nucleotide 42 (A→T or A→C) and nucleotide 96 (G→A), where these nucleotides are presented in positive strand, antigenomic, message sense; and
(2) at least one attenuating mutation in the RNA polymerase gene selected from the group consisting of nucleotide changes which produce changes in an amino acid selected from the group consisting of residues 331 (isoleucine→threonine), 1409 (alanine→threonine), 1624 (threonine→alanine), 1649 (arginine→methionine), 1717 (aspartic acid→alanine), 1936 (histidine→tyrosine), 2074 (glutamine→arginine) and 2114 (arginine→lysine).

Furthermore, in in published International patent application WO99/49017 (94), which is hereby incorporated by reference, the generation and isolation of recombinantly-generated, attenuated, measles viruses having at least one attenuating mutation in the N, P or C genes or in the F gene-end signal, was disclosed.

Specifically, these mutations comprised:

(1) for the N gene, at least one attenuating mutation selected from the group consisting of nucleotide changes which produce changes in an amino acid selected from the group consisting of residues 129 (glutamine→lysine), 148 (glutamic acid→glycine) and 479 (serine→threonine);

(2) for the P gene, at least one attenuating mutation selected from the group consisting of nucleotide changes which produce changes in an amino acid selected from the group consisting of residues 225 (glutamic acid→glycine), 275 (cysteine→tyrosine) and 439 (leucine→proline);

(3) for the C gene, at least one attenuating mutation selected from the group consisting of nucleotide changes which produce changes in an amino acid selected from the group consisting of residues 73 (alanine→valine), 104 (methionine→threonine) and 134 (serine→tyrosine); and (4) for the F gene-end signal (the cis-acting transcription termination signal), the change at nucleotide 7243 (T→C), where these nucleotidesare presented in positive strand, antigenomic, that is, message (coding) sense.

Individual or combinations of attenuating mutations from either or both of these sets of mutations can be incorporated into the Morbilliviruses of this invention, including specifically those with at least one mutation in the region corresponding to amino acids 112–134 of the V protein, as well as to those containing both such a mutation in amino acids 112–134 and a mutation in or deletion of at least a portion of the C-terminal region beginning at amino acid 231.

The viruses of this invention are used to formulate a vaccine or immunogenic composition. To do so, the virus is adjusted to an appropriate concentration and formulated with any suitable adjuvant, diluent or carrier. Physiologically acceptable media may be used as carriers and/or diluents. These include, but are not limited to: water, an appropriate isotonic medium, glycerol, ethanol and other conventional solvents, phosphate buffered saline and the like. Suitable adjuvants include, but are not limited to aluminum phosphate, aluminum hydroxide, MPL™ (3-O-deacylated monophosphoryl lipid A; RIBI ImmunoChem Research, Inc., Hamilton, Mont., now Corixa), synthetic lipid A analogs such as 529 (Corixa), Stimulon™ QS-21 (Aquila Biopharmaceuticals, Framingham, Mass.) and IL-12 (Genetics Institute, Cambridge, Mass.).

In one embodiment of this invention, the formulation including the Morbillivirus is intended for use as a vaccine or immunogenic composition. The virus may be mixed with cryoprotective additives or stabilizers such as proteins (e.g., albumin, gelatin), sugars (e.g., sucrose, lactose, sorbitol), amino acids (e.g., sodium glutamate), saline, or other protective agents. This mixture is maintained in a liquid state, or is then dessicated or lyophilized for transport and storage and mixed with water immediately prior to administration.

Formulations comprising the Morbilliviruses of this invention are useful to immunize a human or other vertebrate subject to induce protection against infection by the wild-type counterpart of the virus. Thus, this invention further provides a method of immunizing a subject to induce protection against infection by a Morbillivirus by administering to the subject an effective immunizing amount of a formulation of the vaccine or immunogenic composition incorporating a version of that virus generated as described hereinabove.

A sufficient amount of the vaccine or immunogenic composition in an appropriate number of doses is administered to the subject to elicit an immune response. Persons skilled in the art will readily be able to determine such amounts and dosages. Administration may be by any conventional effective form, such as intranasally, parenterally, orally, or topically applied to any mucosal surface such as intranasal, oral, eye, lung, vaginal or rectal surface, such as by an aerosol spray. The preferred means of administration is by intranasal administration.

All patents and publications cited herein are hereby incorporated by reference.

In order that this invention may be better understood, the following examples are set forth. The examples are for the purpose of illustration only and are not to be construed as limiting the scope of the invention.

EXAMPLES

Example 1

Cells and Virus

HEp2 cells were grown in Dulbecco's modified Eagle's medium (DMEM) supplemented with 10% fetal bovine serum. Chicken embryo fibroblasts (CEFs; SPAFAS, Inc) were maintained in the same media. The attenuated strain of vaccinia virus that expresses phage T7 RNA-polymerase (MVA/T7; 62) was grown in CEFs. Plaque assays were performed also on CEFs.

Example 2

Recombinant DNA

The measles virus N, P and L protein expression clones (FIG. 1A) were each prepared from infected-cell total RNA by reverse transcription and PCR amplification (RT/PCR) with gene-specific primers, followed by cloning into an appropriate T7 RNA polymerase-dependent expression vector (61). Vero cells were infected with the Edmonston wild-type strain of measles virus, and when about 70% or more of the cells exhibited a cytopathic effect, RNA was prepared by the gaunidinium-phenol extraction method (95). RT/PCR was performed with avian myoblastosis virus RT and Pwo polymerase contained in the one-tube Titan amplification kit (Roche Molecular Biology). The RT step was performed for 30–60 minutes at 47° C., followed by 30–35 cycles of PCR amplification. Amplified DNA fragments were cloned into a T7 expression plasmid (FIG. 1; (61,83)) with the translation initiation codon placed in the NcoI site of the vector. Cloned DNAs were checked by cycle-sequencing (96) and nucleotide substitution errors were corrected by oligonucleotide mutatgenesis using the Morph kit (5prime-3prime, Inc.) or by replacing subfragments with newly-amplified DNA fragments as described previously (96).

The initial V protein expression clone was prepared by PCR amplification from an Edmonston wild-type full-length cDNA clone using primers flanking the V protein coding region. The amplified DNA was cloned into the T7 expression vector and the additional G nucleotide residue required to generate the V gene frameshift was added at the editing site (18) by oligonucleotide-directed mutatgenesis. Wild-type and mutant V protein expression vectors were also prepared with an influenza virus hemmaglutinin epitope tag (HA tag; (67)) at the amino terminus. The T7 vector plasmid was modified to include a sequence that includes an intiation codon and encodes the HA epitope tag (CC ATG GCT TAT CCT TAT GAC GTG CCT GAC TAT GCC)(SEQ ID NO:5), followed by a polylinker (plasmid pT7/HA). The V protein coding region was cloned with the HA tag at the amino terminus. This served to replace the V protein initiator methionine codon, resulting in the generation of a plasmid designated pMV-haV-wt. V protein mutants were prepared in the pMV-haV-wt backbone by oligonucleotide-directed or deletion mutagenesis.

The primer designed to amplify the 5' end of the P and V coding regions (CGGCCATGGCAGAAGAGACAGGCACGCCACGT AAAAAACGGAC)(SEQ ID NO:6) contained two base changes (underlined) to disrupt the downstream C protein open reading frame. These changes were silent with respect to the P and V open reading frames. The same nucleotide changes were carried over to the pT7MV-haV constructs.

For all protein expression constructs, the cDNA insert was cloned 3' of an internal ribosome entry site (IRES) to facilitate translation of the T7 RNA polymerase transcript. A stretch of 50 adenosine residues was located at the 3' end, followed by a T7 RNA polymerase terminator. Both the P and V expression vectors contained base substitutions designed to disrupt translation initiation from the downstream C protein open reading frame.

The measles virus minireplicon (pMVwt107-CAT, FIG. 1B) was a derivative of pMV107-CAT (63). Plasmid pMV107-CAT contained the leader sequence found in vaccine strains of measles virus (60) and was converted to plasmid pMV107wt-CAT (which contained the wild-type leader) using oligonucleotide-directed mutatgenesis.

Example 3

Transient Expression Experiments

Figure 1B:
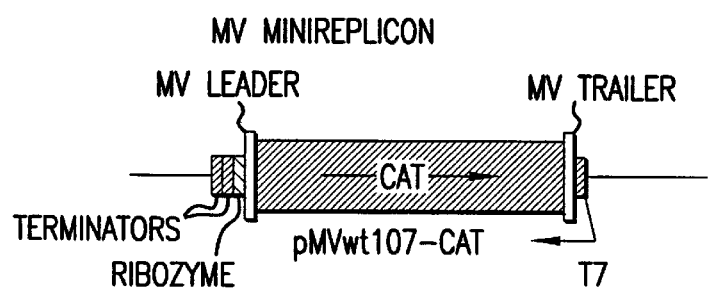
FIG. 1B depicts the minireplicon which was derived from pMV107-CAT (63). The Edmonston measles virus vaccine leader sequence in pMV107-CAT was converted to the wild-type sequence (60). Transcription of the minireplicon plasmid DNA by T7 RNA polymerase generated a negative-sense RNA minireplicon copy in transfected cells.
Figure 1C:
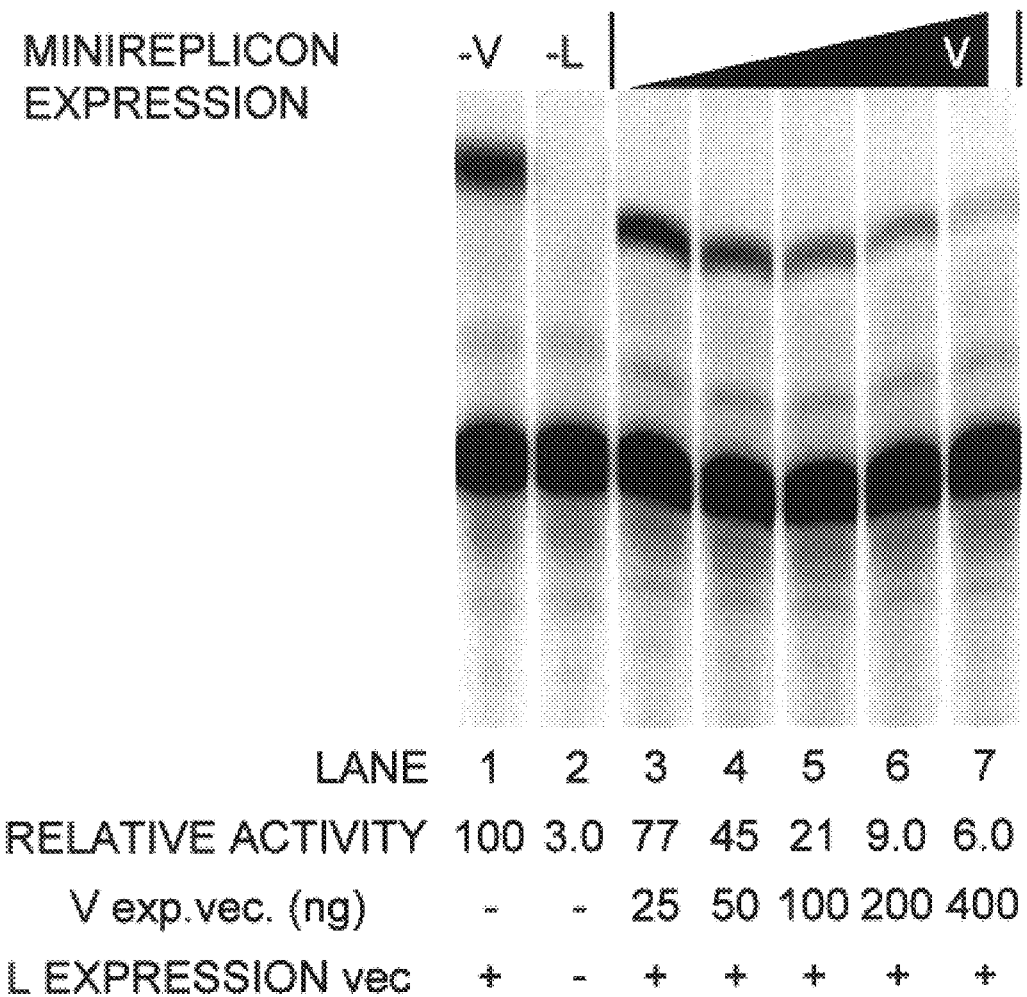
FIG. 1C depicts a CAT assay that demonstrated the effect of V protein expression on minireplicon activity in a transient expression assay. Lane 1 was the positive control obtained from cells that were transfected with all plasmid vectors (N, P and L) necessary to drive minireplicon expression. Lane 2 was identical to lane 1, except that the cells were transfected with all plasmids except the L polymerase vector. In lanes 3 through 7, increasing amounts of V protein expression vector was included in the transfection. The total mass of transfected DNA was held constant by including the appropriate amount of vector DNA without an insert. Relative CAT activity was calculated based on 100% activity in lane 1.

Analysis of transient minireplicon expression was performed essentially as described previously (96) using varying amounts of viral protein expression vectors (FIG. 1B) and a measles virus minireplicon containing the CAT reporter gene (FIG. 1B). The measles virus minireplicon was a derivative of pMV107-CAT (63) containing the CAT reporter gene and the measles leader sequence from the Edmonston wild-type strain of measles virus (60). HEp2 cells in six-well plates were used for transfection when the cells were about 70–90% confluent. Transfection mixes were prepared by combining minireplicon DNA (50–200 ng pMVwt107-CAT) and expression plasmids (400 ng pMVwt-N, 300 ng pMVwt-P[C−], 100 ng pMVwt-L) in 200 μl of serum-free OptiMEM. V protein expression plasmids were included in this mix according to the amounts ranging from 25–400 ng, as specified in FIG. 1C. Lipofectace (12–15 μl; Invitrogen/Life Technologies) was added to the DNA-medium mixture and incubated for 20 to 30 minutes at room temperature. A separate MVA/T7 mixture was prepared in sufficient quantity to provide 0.8 ml of serum-free OptiMEM containing enough MVA/T7 to infect each well of cells to be transfected with about 2 pfu per cell. Before initiating transfection, the DNA-medium-Lipofectace transfection mix was combined with 800 μl of the MVA/T7-media mix and mixed gently by pipetting. Next, the culture media was removed from the cell monolayers and the combined 1 ml transfection mixture was added to the cells.

After overnight incubation, the transfection mixture and media were replaced with DMEM supplemented with 10% FBS and the cells were incubated an additional day. About 48 hours after the start of transfection, the cells were harvested and extracts prepared for analysis of CAT activity as described previously (96). The expression of CAT is shown in FIG. 1C. In some experiments, proteins in crude cell extracts were analyzed by Western blotting to monitor protein expression (97). Transfected cells were lysed using TN buffer (50 mM Tris [pH 7.4], 150 mM NaCl) supplemented with 0.2% NP40. The cell extracts were cleared by centrifugation to remove nuclei and an equal volume of Laemmli sample buffer (62.5 mM Tris [pH 6.8], 25% glycerol, 2% SDS, 0.01% bromophenol blue) was added to the cytoplasmic extract. The samples were adjusted to contain approximately 2.5% P-mercaptoethanol and then boiled. SDS polyacrylamide gel electrophoresis and electroblotting were performed using standard protocols (97). Epitope-tagged V protein was detected using either mouse monoclonal antibody 12CA5 (Roche Molecular Biology) or rat monoclonal antibody 3F10 (Roche Molecular Biology). Detection was performed with a peroxidase-conjugated secondary antibody (Sigma) and chemilumenesnce reagents (Roche Molecular Biology or New England Nuclear).

Example 4

Repression of Minireplicon Expression by Mutant Measles Virus V Proteins

The transient minireplicon expression CAT assay described in Example 3 was repeated using varying amounts of the measles virus V protein mutants haV-1 to haV-8, which have the following differences from the wild-type sequence (haV-wt) (see FIG. 3):

haV-1 Deletion of amino acids 231–299 haV-2 Mutation of glutamic acid at amino acid 225 to glycine haV-3 Mutations of lysines at amino acids 229 and 230 to alanines haV-4 Mutations of lysine and threonine at amino acids 204 and 209 to alanines haV-5 Mutations of tyrosine and aspartic acid at amino acids 113 and 114 to alanines haV-6 Mutations of leucine and glutamine at amino acids 100 and 101 to alanines haV-7 Mutations of glutamic acid and cysteine at amino acids 14 and 15 to alanines haV-8 Mutations of glutamic acid at amino acids 3 and 4 to alanines Either 200 or 400 ng of each V plasmid (encoding wild-type or haV-1 through haV-8 V protein) was used and the relative CAT activity was measured as a percentage of the activity resulting from a transfection performed without any V protein expression vector (lane 2). The results are depicted in FIG. 4A. A lower percentage correlates with a higher degree of repression of CAT expression. The expression of V protein was monitored by a Western blot which was analyzed with anti-HA antibody (FIG. 4B).

The CAT assay was repeated using increasing amounts (100 ng to 1 μg) of the V plasmid encoding hav-1 and the relative activities are depicted in FIG. 4C.

Example 5

RNA Binding Assays

Figure 5A:
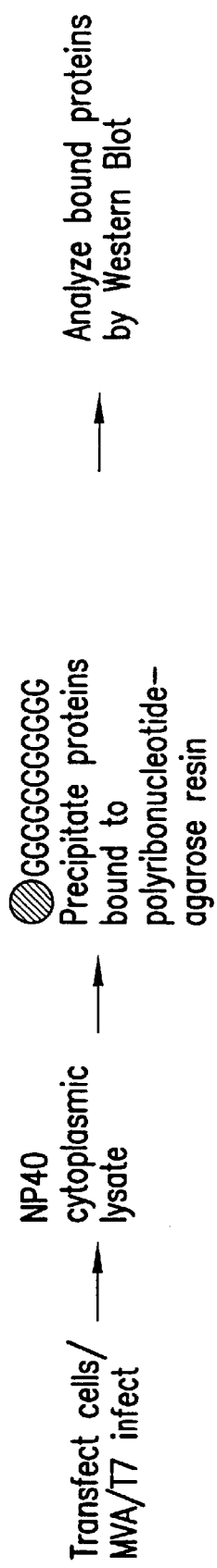
FIG. 5 depicts the RNA binding activity associated with measles virus V protein. Crude cytoplasmic extracts prepared from transfected cells by NP40 lysis were analyzed for RNA binding activity using agarose beads linked to polyribonucleotide homopolymers. A flow diagram illustrating the procedure is shown in FIG. 5A.
FIG. 5B depicts Western blots used to examine proteins captured on the polyribonucleotide resins. Cells were transfected using the same conditions as used for minireplicon experiments (lanes 1–8), except that in some transfections the cells were transfected only with haV expression vector (lanes 9–12). Lanes 1–4 depict an analysis of N protein binding to the four different polynucleotide resins. Lanes 5–12 depict an analysis of the bound fraction for haV protein. Similarly, lanes 9–16 depict an analysis of V protein that bound to poly(G) in the presence of EGTA (EG), EDTA (ED), or yeast RNA (RNA).

RNA binding assays (74,76,77) were performed to evaluate the binding of measles virus V protein to RNA, using agarose resins couple with polyribonucleotides (Sigma). Transfected cells were lysed as described above using TN buffer supplemented with 0.5% NP40, 5% glycerol, 1 mM $MgCl_2$, 1 mM $ZnCl_2$ and protease inhibitor cocktail (Roche Molecular Biology). Agarose resins containing polyribonucleotides (approximately 25–50 µl of settled volume of beads) were added to the cleared cell lysate and incubated 30–60 minutes at 4° C. with rocking. After incubation, the resins were washed three times to remove unbound proteins. Proteins were eluted from the resins by boiling in Laemmli buffer supplemented with 2.5% β-mercaptoethanol. The procedure is summarized by the flow diagram of FIG. 5A. Proteins captured by the polynucleotide resins were analyzed by Western blotting as described above. The assay was carried out first with wild-type V protein, and then with haV-1 through haV-11. The mutants haV-1 through haV-8 are as described above; the mutants haV-9 through haV-11 have the following differences from the wild-type sequence (haV-wt) (see FIG. 3):

haV-9 Deletion of amino acids 1–20 haV-10 Deletion of amino acids 208–230 haV-11 Deletion of amino acids 1–20 and 208–230

Figure 5B:
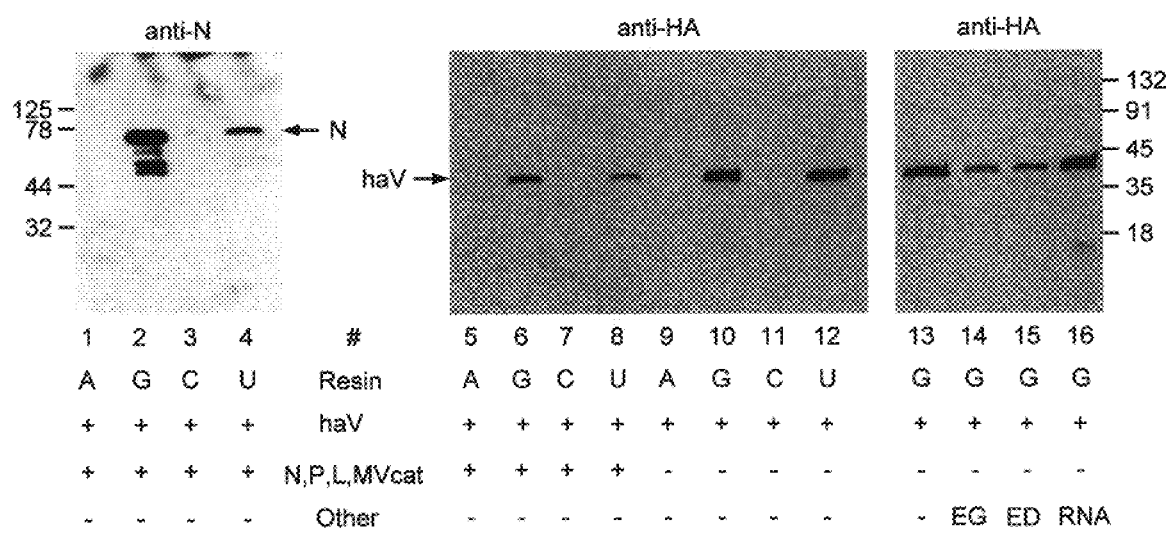

The results are depicted in FIGS. 5B (wild-type) and 6 (mutants).

Example 6

Repression of Minireplicon Expression by Additional CR2 Mutant Measles Virus V Proteins The transient minireplicon expression CAT assay described in Examples 3 and 4 was repeated using the measles virus V protein CR2 mutants haV-5 and haV-23 to haV-25, which have the following differences from the wild-type sequence (haV)(SEQ ID NO:7) in CR2 (amino acids 100–140; see FIG. 7):

haV-5 Mutations of tyrosine and aspartic acid at amino acids 113 and 114 to alanines (SEQ ID NO:8)

haV-23 Deletion of amino acids 112 to 134 (SEQ ID NO:9)

haV-24 Mutations of aspartic acid and histidine at amino acids 114 and 115 to alanines (SEQ ID NO:10)

haV-25 Mutations of tyrosine, aspartic acid and histidine at amino acids 113 to 155 (SEQ ID NO:11)

Four hundred nanograms of each V plasmid (encoding wild-type, haV-5 or haV-23 through haV-25 V protein) was used and the relative CAT activity was measured as a percentage of the activity resulting from a transfection performed without any V protein expression vector (bar 1). The results are depicted in FIG. 8. A lower percentage correlates with a higher degree of repression of CAT expression.

Example 7

Repression of Minireplicon Expression by Additional C-Terminal Mutant Measles Virus V Proteins The transient minireplicon expression CAT assay described in Examples 3 and 4 was repeated using the measles virus V protein mutants haV-1 and haV-12 to haV-22, which have the following differences from the wild-type sequence (haV)(SEQ ID NO:7) in the C-terminus (amino acids 220–299; see FIG. 9):

haV-1 Deletion of amino acids 232 to 299 (SEQ ID NO:13)

haV-12 Mutations of cysteines at amino acids 251 and 255 to alanines (SEQ ID NO:14)

haV-13 Mutations of cysteines at amino acids 269 and 272 to alanines (SEQ ID NO:15)

haV-14 Deletion of amino acids 279 to 299 (SEQ ID NO:16)

haV-15 Deletion of amino acids 267 to 299 (SEQ ID NO:17)

haV-16 Deletion of amino acids 250 to 299 (SEQ ID NO:18)

haV-17 Deletion of amino acids 243 to 299 (SEQ ID NO:19)

haV-18 Deletion of amino acids 236 to 299 (SEQ ID NO:20)

haV-19 Deletion of amino acids 229 to 299 (SEQ ID NO:21)

haV-20 Mutations of arginines at amino acids 233 and 234 to alanines (SEQ ID NO:22)

haV-21 Mutations of arginines at amino acids 233 and 234 to aspartic acid (SEQ ID NO:23)

haV-22 Deletion of amino acids 229 to 237 (SEQ ID NO:24)

Four hundred nanograms of each V plasmid (encoding wild-type, haV-1 or haV-12 through haV-22 V protein) was used and the relative CAT activity was measured as a percentage of the activity resulting from a transfection performed without any V protein expression vector (bar 1). The results are depicted in FIG. 10. A lower percentage correlates with a higher degree of repression of CAT expression.

Bibliography

1. Black, F. L., et al., *Am. J. Epidemiol.*, 124, 442–452 (1986).

2. Lennon, J. L., and Black, F. L., *J. Pediatrics*, 108, 671–676 (1986).

3. Pabst, H. F., et al., *Pediatr. Infect. Dis. J.*, 11, 525–529 (1992).

4. Centers for Disease Control, *MMWR*, 40, 369–372 (1991).

5. Centers for Disease Control, *MMWR*, 41:S6, 1–12 (1992).

6. King, G. E., et al., *Pediatr. Infect. Dis. J.*, 10, 883–887 (1991).

7. Rota, J. S., et al., *Virology*, 188, 135–142 (1992).

8. Griffin, D. E., and Bellini, W. J., pages 1267–1312 of Volume 1, *Fields Virology*, B. N. Fields, et al., Eds. (3rd ed., Raven Press, 1996).

9. Lamb, R. A., and Kolakosky, D., pages 1177–1204 of Volume 1, *Fields Virology*, B. N. Fields, et al., Eds. (3rd ed., Raven Press, 1996).

10. Birrer, M. J., et al., *Virology*, 108, 381–390 (1981)

11. Birrer, M. J., et al., *Nature*, 293, 67–69 (1981).

12. Norby, E., et al., pages 481–507, in *The Paramyxoviruses*, D. Kingsbury, Ed. (Plenum Press, 1991).

13. Peebles, M. E., pages 427–456, in *The Paramyxoviruses*, D. Kingsbury, Ed. (Plenum Press, 1991).

14. Egelman, E. H., et al., *J. Virol.*, 63, 2233–2243 (1989).

15. Udem, S. A., et al., *J. Virol. Methods*, 8, 123–136 (1984).

16. Udem, S. A., and Cook, K. A., *J. Virol.*, 49, 57–65 (1984).

17. Moyer, S. A., and Horikami, S. M., pages 249–274, in *The Paramyxoviruses*, D. Kingsbury, Ed. (Plenum Press, 1991).

18. Cattaneo, R., et al., *Cell*, 56, 759–764 (1989).

19. Nagai, Y., *Rev. Med. Virol.*, 9, 83–99 (1999).

20. Bellini, W. J., et al., *J. Virol.*, 53, 908–919 (1985).

21. Baron, M. D., and Barrett, T., *J. Virol.*, 74, 2603–2611 (2000).

22. Delenda, C., et al., *Virology*, 242, 327–337 (1998).

23. Durbin, A. P., et al., *Virology*, 261, 319–330 (1999).

24. Kato, A., et al., *J. Virol.*, 71, 7266–7272 (1997).

25. Schneider, H., et al., *Virology*, 227, 314–322 (1997).

26. Kato, A., et al., *EMBO J.*, 16, 578–587 (1997).

27. Tober, C., et al., *J. Virol.*, 72, 8124–8132 (1998).

28. Valsamakis, A., et al., *J. Virol.*, 72, 7754–7761 (1998).

29. Patterson, J. B., et al., *Virology*, 267, 86–89 (2000).

30. Parks, C. L., et al., *J. Virol.*, 75, 910–920 (2001).

31. Takeda, M., et al., *J. Virol.*, 72, 8690–8696 (1998).

32. Bankamp, B., et al., *Virology*, 216, 272–277 (1996).

33. Curran, J., et al., *J. Virol.*, 69, 849–855 (1995). 34. Harty, R. N., and Palese, P., *J. Gen Virol.*, 76, 2863–2867 (1995).

35. Horikami, S. M., et al., *Virology*, 222, 383–390 (1996).

36. Nishio, M., et al., *J. Gen. Virol.*, 77, 2457–2463 (1996).

37. Randall, R. E., and Bermingham, A., *Virology*, 224, 121–129 (1996).

38. Shaji, D., and Shaila, M. S., *Virology*, 258, 415–424 (1999).

39. Watanabe, N., et al., *Medical Microbiology & Immunology*, 185, 89–94 (1996).

40. Precious, B., et al., *J. Virol.*, 69, 8001–8010 (1995).

41. Watanabe, N., et al., *J. Gen. Virol.*, 77, 327–328 (1996).

42. Lin, G.Y., et al *Virology*, 249, 189–200 (1998).

43. Liston, P., et al., *Virus Res.*, 38, 241–259 (1995).

44. Didcock, L., et al., *J. Virol.*, 73, 9928–9933 (1999).

45. Curran, J., et al *EMBO J.*, 10, 3079–3085 (1991).

46. Baron, M. D., et al., *J. Gen. Virol.*, 74, 299–304 (1993).

47. Thomas, S. M., et al., *Cell*, 54, 891–902 (1988).

48. Borden, K. L. B., and Freemont, P. S., *Curr. Opinion Stuctural Biol.*, 6, 395–401 (1996).

49. Choo, Y., and Klug, A., *Curr. Opinion Structural Biol.*, 7, 117–125 (1997).

50. O'Halloran, T., V., *Science*, 261, 715–725 (1993).

51. Liston, P., and Briedis, D. J., *Virology*, 198, 399–404 (1994).

52. Paterson, R. G., et al *Virology*, 208, 121–131 (1995).

53. Steward, M., et al., *Archives Virol.*, 140, 1321–1328 (1995).

54. Blumberg, B., et al., pages 235–247, in *The Paramyxoviruses*, D. Kingsbury, Ed. (Plenum Press, 1991).

55. Berrett, T., et al., pages 83–102, in *The Paramyxoviruses*, D. Kingsbury, Ed. (Plenum Press, 1991).

56. Tordo, N., et al., *Sem. in Virology*, 3, 341–357 (1992).

57. Cattaneo, R., et al *EMBO J.*, 6, 681–688 (1987).

58. Castaneda, S. J., and Wong, T. C., *J. Virol.*, 63, 2977–2986 (1989).

59. Castaneda, S. J., and Wong, T. C., *J. Virol.*, 64, 222–230 (1990).

60. Parks, C. L., et al., *J. Virol.*, 75, 921–933 (2001).

61. Moss, B., et al., *Nature*, 348, 91–92 (1990).

62. Wyatt, L. S., et al *Virology*, 210, 202–205 (1995).

63. Sidhu, M. S., et al *Virology*, 208, 800–807 (1995).

64. Huber, M., et al *Virology*, 185, 299–308 (1991).

65. Alber, T., *Curr. Opin. Genetics Dev.*, 2, 205–210 (1992).

66. Baxevanis, A. D., and Vinson, C. R., *Curr. Opion. Genetics Dev.*, 3, 278–285 (1993).

67. Kolodziej, P. A., and Young, R. A., *Methods Enzymology*, 194, 508–519 (1991).

68. Bass, S. H., et al., *Proc. Natl. Acad. Sci., USA*, 88, 4498–4502 (1991).

69. Diamond, S. E., and Kirkegaard, K., *J. Virol.*, 68, 863–876 (1994).

70. Gibbs, C. S., and Zoller, M. J., *J. Biol. Chem.*, 266, 8923–8931 (1991).

71. Giniger, E., and Ptashne, M., *Nature*, 330, 670–672 (1987).

72. Sedlmeirer, R., and Neubert, W. J., *Adv. Virus Res.*, 50, 101–139 (1998).

73. Lin, G. Y., et al *Virology*, 238, 460–469 (1997).

74. Elenbaas, B., et al., *Molecular Medicine*, 2, 439–451 (1996).

75. Kiledjian, M., and Dreyfuss, G., *EMBO J.*, 11, 2655–2664 (1992).

76. Siomi, H., et al., *Cell*, 74, 291–298 (1993).

77. Swanson, M., and Dreyfuss, G., *Mol. Cell. Biol.*, 8, 2237–2241 (1988).

78. Mitchell, P., and Tjian, R., *Science*, 245, 371–378 (1989).

79. Conzelmann, K. K., *Annual Review of Genetics*, 32, 123–162 (1998).

80. Radecke, F., and Billeter, M. A., *Rev. Med. Virology*, 7, 49–63 (1997).

81. Roberts, A., and Rose, J. K., *Virology*, 247, 1–6 (1998).

82. Garcin, D., et al *EMBO J.*, 14, 6087–6094 (1995).

83. Radecke, F., et al *EMBO J.*, 14, 5773–5784 (1995).

84. Collins, P. L., et al., *Proc. Natl. Acad. Sci., USA*, 92, 11563–11567 (1995).

85. Published International Application No. WO 98/53078.

86. Published European Patent Application No. 702,085.

87. Rota, J. S., et al., *Virus Res.*, 31, 317–330 (1994).

88. Published International Application No. WO 97/06270.

89. Baron, M. D., and Barrett, T., *J. Virology*, 71, 1265–1271 (1997).

90. Kato, A., et al., *Genes to Cells*, 1, 569–579 (1996).

91. Shaffer, M. F., et al., *J. Immunol.*, 41, 241–256 (1941).

92. Enders, J. F., et al., *N. Engl. J. Med.*, 263, 153–159 (1960).

93. Published International Application No. WO 98/13501.

94. Published International Application No. WO 99/49017.

95. Chomczynski, P., and Sacchi, N., *Analytical Biochem.*, 162, 156–159 (1987).

96. Parks, C. L., et al., *J. Virol.*, 73, 3560–3566 (1999).

97. Ausubel, F. M., et al., eds., Current Protocols in Molecular Biology (Greene Publishing Associates and Wiley Interscience, New York, N.Y. 1987).

What is claimed is:

1. An isolated, recombinantly-generated, nonsegmented, negative-sense, single-stranded RNA virus of the genus Morbillivirus having at least one mutation in the region corresponding to amino acids 112–134 of a Morbillivirus V protein, wherein the mutation in the region corresponding to amino acids 112–134 of a Morbillivirus V protein is selected from the group consisting of the mutation of amino acids 113 and 114.

2. The Morbillivirus of claim 1 wherein the virus is selected from the group consisting of measles virus, canine distemper virus, rinderpest virus, pestedes-des-petits ruminants virus, dolphin morbillivirus and phocine distemper virus.

3. The Morbillivirus of claim 1 wherein the mutation is at amino acid 113.

4. The Morbillivirus of claim 3 wherein the mutation at amino acid 113 is from tyrosine to alanine.

5. The Morbillivirus of claim 1 wherein the mutation is at amino acid 114.

6. The Morbillivirus of claim 5 wherein the mutation at amino acid 114 is from aspartic acid to alanine.

7. The Morbillivirus of claim 1 wherein there is a mutation at both amino acids 113 and 114.

8. The Morbillivirus of claim 7 wherein the mutation at amino acid 113 is from tyrosine to alanine and the mutation at amino acid 114 is from aspartic acid to alanine.

9. The Morbillivirus of claim 2 wherein the virus is measles virus.

10. The measles virus of claim 3 which further comprises a mutation in or deletion of at least a portion of the carboxy-terminal (C-terminal) region corresponding to amino acids 231–299 of the measles virus V protein.

11. The measles virus of claim 10 wherein the mutation in the C-terminal region is at each of amino acids 233 and 234.

12. The measles virus of claim 11 wherein the mutation at each of amino acids 233 and 234 is from arginine to alanine.

13. The measles virus of claim 11 wherein the mutation at each of amino acids 233 and 234 is from arginine to aspartic acid.

14. The measles virus of claim 10 wherein the deletion is selected from the group consisting of the deletion of amino acids 232 to 299, 279 to 299, 267 to 299, 250 to 299, 243 to 299 and 236 to 299.

15. The measles virus of claim 14 wherein the deletion is from amino acids 232 to 299.

16. The measles virus of claim 15 wherein the deletion extends upstream from the C-terminal region and is from amino acids 229 to 299.

17. The measles virus of claim 3 which further comprises:

(a) at least one attenuating mutation in the 3' genomic promoter region selected from the group consisting of nucleotide 26 (A→T), nucleotide 42 (A→T or A→C) and nucleotide 96 (G→A), where these nucleotides are presented in positive strand, antigenomic, message sense; and (b) at least one attenuating mutation in the RNA polymerase gene selected from the group consisting of nucleotide changes which produce changes in an amino acid selected from the group consisting of residues 331 (isoleucine→threonine), 1409 (alanine→threonine), 1624 (threonine→alanine), 1649 (arginine→methionine), 1717 (aspartic acid→alanine), 1936 (histidine→tyrosine), 2074 (glutamine→arginine) and 2114 (arginine→lysine).

18. The measles virus of claim 3 which further comprises at least one attenuating mutation selected from the group consisting of:

(a) for the N gene, nucleotide changes which produce changes in an amino acid selected from the group consisting of residues 129 (glutamine→lysine), 148 (glutamic acid→glycine) and 479 (serine→threonine);

(b) for the P gene, nucleotide changes which produce changes in an amino acid selected from the group consisting of residues 225 (glutamic acid→glycine), 275 (cysteine→tyrosine) and 439 (leucine→proline);

(c) for the C gene, nucleotide changes which produce changes in an amino acid selected from the group consisting of residues 73 (alanine→valine), 104 (methionine→threonine) and 134 (serine→tyrosine); and (d) for the F gene-end signal, the change at nucleotide 7243 (T→C), where these nucleotides are presented in positive strand, antigenomic, message sense.

19. The measles virus of claim 10 which further comprises:

(a) at least one attenuating mutation in the 3' genomic promoter region selected from the group consisting of nucleotide 26 (A→T), nucleotide 42 (A→T or A→C) and nucleotide 96 (G→A), where these nucleotides are presented in positive strand, antigenomic, message sense; and (b) at least one attenuating mutation in the RNA polymerase gene selected from the group consisting of nucleotide changes which produce changes in an amino acid selected from the group consisting of residues 331 (isoleucine→threonine), 1409 (alanine→threonine), 1624 (threonine→alanine), 1649 (arginine→methionine), 1717 (aspartic acid→alanine), 1936 (histidine→tyrosine), 2074 (glutamine→arginine) and 2114 (arginine→lysine).

20. The measles virus of claim 10 which further comprises at least one attenuating mutation selected from the group consisting of:

(a) for the N gene, nucleotide changes which produce changes in an amino acid selected from the group consisting of residues 129 (glutamine→lysine), 148 (glutamic acid→glycine) and 479 (serine→threonine);

(b) for the P gene, nucleotide changes which produce changes in an amino acid selected from the group consisting of residues 225 (glutamic acid→glycine), 275 (cysteine→tyrosine) and 439 (leucine→proline);

(c) for the C gene, nucleotide changes which produce changes in an amino acid selected from the group consisting of residues 73 (alanine→valine), 104 (methionine→threonine) and 134 (serine→tyrosine); and (d) for the F gene-end signal, the change at nucleotide 7243 (T→C), where these nucleotides are presented in positive strand, antigenomic, message sense.

21. The Morbillivirus of claim 2 wherein the virus is canine distemper virus.

22. The canine distemper virus of claim 21 which further comprises a mutation in or deletion of at least a portion of the C-terminal region corresponding to amino acids 231–299 of the canine distemper virus V protein.

23. The Morbillivirus of claim 2 wherein the virus is rinderpest virus.

24. The rinderpest virus of claim 23 which further comprises a mutation in or deletion of at least a portion of the C-terminal region corresponding to amino acids 231–299 of the rinderpest virus V protein.

25. The Morbillivirus of claim 2 wherein the virus is dolphin morbillivirus.

26. The dolphin morbillivirus of claim 25 which further comprises a mutation in or deletion of at least a portion of the C-terminal region corresponding to amino acids 231–303 of the rinderpest virus V protein.

27. An immunogenic composition comprising an isolated, recombinantly-generated, nonsegmented, negative-sense, single-stranded RNA virus of the genus Morbillivirus having at least one mutation in the region corresponding to amino acids 112–134 of a Morbillivirus V protein, wherein the mutation in the region corresponding to amino acids 112–134 of a Morbillivirus V protein is selected from the group consisting of the mutation of amino acids 113 and 114, together with a diluent or carrier.

28. A method for immunizing an individual to induce protection against a nonsegmented, negative-sense, single-stranded RNA virus of the genus Morbillivirus which comprises administering to the individual the immunogenic composition of claim 27.

29. The immunogenic composition of claim 27 which further comprises an-adjuvant.

30. A method for immunizing an individual to induce protection against a nonsegmented, negative-sense, single-stranded RNA virus of the genus Morbillivirus which comprises administering to the individual the immunogenic composition of claim 29.

31. A method for reducing the repression caused by a V protein of the genus Morbillivirus which comprises inserting at least one mutation in the region corresponding to amino acids 112–134 of a Morbillivirus V protein, wherein the mutation in the region corresponding to amino acids 112–134 of a Morbillivirus V protein is selected from the group consisting of the mutation of amino acids 113 and 114.

32. An isolated nucleotide sequence encoding a Morbillivirus V protein which has been modified by inserting at least one mutation in the region corresponding to amino acids 112–134 of a Morbillivirus V protein, wherein the mutation in the region corresponding to amino acids 112–134 of a Morbillivirus V protein is selected from the group consisting of the mutation of amino acids 113 and 114.

33. A composition which comprises a transcription vector comprising an isolated nucleic acid molecule encoding a genome or antigenome of a Morbillivirus, wherein the portion of the isolated nucleic acid molecule encoding the V protein has been modified so as to insert at least one mutation in the region corresponding to amino acids 112–134 of a Morbillivirus V protein, wherein the mutation in the region corresponding to amino acids 112–134 of a Morbillivirus V protein is selected from the group consisting of the mutation of amino acids 113 and 114, together with at least one expression vector which comprises at least one isolated nucleic acid molecule encoding the trans-acting proteins N, P and L necessary for encapsidation, transcription and replication, whereby upon expression an infectious Morbillivirus is produced.

34. A method for producing an infectious Morbillivirus which comprises transforming, infecting or transfecting host cells with the at least two vectors of claim 33 and culturing the host cells under conditions which permit the co-expression of these vectors so as to produce the infectious Morbillivirus.

* * * * *